US007271173B2

(12) United States Patent
Neumeyer et al.

(10) Patent No.: US 7,271,173 B2
(45) Date of Patent: Sep. 18, 2007

(54) **MIXED *KAPPA/MU* OPIOIDS AND USES THEREOF**

(75) Inventors: John L. Neumeyer, Wayland, MA (US); Ao Zhang, Malden, MA (US)

(73) Assignee: The McLean Hospital Corporation, Boston, MA (US)

( * ) Notice: Subject to any disclaimer, the term of this patent is extended or adjusted under 35 U.S.C. 154(b) by 0 days.

(21) Appl. No.: 10/716,100

(22) Filed: Nov. 18, 2003

(65) Prior Publication Data

US 2004/0259901 A1 Dec. 23, 2004

Related U.S. Application Data

(60) Provisional application No. 60/427,109, filed on Nov. 18, 2002, provisional application No. 60/461,157, filed on Apr. 8, 2003.

(51) Int. Cl.
*A61K 31/4365* (2006.01)
*A61K 31/437* (2006.01)
*C07D 221/18* (2006.01)

(52) U.S. Cl. .................. 514/281; 514/282; 546/43
(58) Field of Classification Search .............. 546/43; 514/281, 282
See application file for complete search history.

(56) References Cited

U.S. PATENT DOCUMENTS

| | | | |
|---|---|---|---|
| 3,853,889 A | 12/1974 | Monkovic et al. | |
| 3,936,462 A | 2/1976 | Albertson | |
| 3,959,290 A | 5/1976 | Monkovic et al. | |
| 4,154,932 A | 5/1979 | Montzka et al. | |
| 4,228,285 A | 10/1980 | Montzka et al. | |
| 4,246,413 A | 1/1981 | Montzka et al. | |
| 4,277,605 A | 7/1981 | Buyniski et al. | |
| 6,166,211 A | 12/2000 | Cain et al. | |
| 2004/0045562 A1 | 3/2004 | Sapala et al. | |

OTHER PUBLICATIONS

Albertson et al., "Benzomorphans. Structure of a Position Isomer," *J. Med. Chem.*, 21:471-474 (1978).
Archer et al., "Pentazocine. Strong Analgesics and Analgesic Antagonists in the Benzomorphan Series," *J. Med. Chem.* 7:123-127 (1964).
Berke et al., "Addiction, Dopamine, and the Molecular Mechanisms of Memory," *Neuron* 25:515-532 (2000).
Bidlack et al., "8-Carboxamidocydazocine: A Long-Acting, Novel Benzomorphan," *J. Pharm. Exp. Ther.* 302:374-380 (2002).
Fawzi et al., "SCH-202676: An Allosteric Modulator of Both Agonist and Antagonist Binding to G Protein-Coupled Receptors," *Mol. Pharm.* 59:30-37 (2001).
Gutkowska et al., "The Synthesis and Pharmacological Activity of Two New Derivatives of Benzazocine," *Pol. J. Pharmacol. Pharm.* 43:153-163 (1991).

Hayes et al., "A Series of Novel, Highly Potent and Selective Agonists for the κ-opioid Receptor," *Br. J. Pharmacol.* 101:944-947 (1990).
Hayes and Birch, "Reversal by β-Funaltrexamine and 16-Methyl Cyprenorphine of the Antinociceptive Effects of Opioid Agonists in the Mouse and Guinea-Pig," *Neuropharmacology* 27:813-816 (1988).
Jordan et al., "Opioids and Their Complicated Receptor Complexes," *Neuropsychopharmacology* 23:S5-S18 (2000).
Kaczor and Matosiuk, "Non-peptide Opioid Recptor Ligands—Recent Advances. Part I—Agonists," *Curr. Med. Chem.* 9:1567-1589 (2002).
Lambert et al., "Analgesics and Narcotic Antagonists in the Benzomorphan and 8-Oxamorphinan Series. 5.," *J. Med. Chem.* 21:423-427 (1978).
Lemaire et al., "14-β-Methyl-8-Oxacyclorphan (BC-3016), a Morphinan Derivative with High Affinity for Kappa Opioid Receptor: Comparison with Dynorphin-A(1-13)," 64:707-711 (1986).
May and Eddy, "Interesting Pharmacological Properties of the Optical Isomers of α-5,9-Diethyl-2'-hydroxy-2-methyl-6,7-benzomorphan," *J. Med. Chem.* 9:851-852 (1966).
McElroy et al., "Synthesis, Antinociceptive Activity, and Opioid Receptor Profiles of 10-Substituted-6-oxamorphinans," *J. Chem. Soc. Perkin Trans. 1* 1563-1571 (1990).
McKenzie et al., "5-Aryl-3-azabicyclo[3.2.0]heptan-6-one Ketals, Compounds with Morphine-Like Analgesic Activity," *J. Med. Chem.* 27:628-632 (1984).
John L. Neumeyer "Mixed Kappa-Mu Opioids: Synthesis and Evaluation" Abstract for NIH Grant No. 2R01DA014251-04A1, Sep. 1, 2001.
Szmuszkovicz, "U-50,488 and the κ Receptor Part II*: 1991-1998," *Progress in Drug Research* 53:1-51 (1999).
Ucar et al., "2 (3H) -Benzoxazolone and 2(3H)-Benzothiazolone Derivatives: Novel, Potent and Selective δ, Receptor Ligands," *Eur. J. Pharmacol.* 355:267-273 (1997).
Wentland et al., "3-Carboxamido Analogues of Morphine and Naitrexone: Synthesis and Opioid Receptor Binding Properties," *Bioorg. Med. Chem. Lett.* 11:1717-1721 (2001).
Wentland et al., "8-Carboxamidocyclazocine Analogues: Redifining the Structure-Activity Relationships of 2,6-Methano-3-benzazocines," *Bioorg. & Med. Chem. Lett.* 11:623-626 (2001).
Wise, "Neurobiology of Addiction," *Curr. Opin. Neurobiol.* 6:243-251 (1996).
Yokoyama et al., "Syntheses, Analgetic Activity, and Physical Dependence Capacity of 5-Phenyl-6,7-benzomorphan Derivatives," *J. Med. Chem.* 22:537-553 (1979).
Zhang et al., "Synthesis of Aminothiazole Derived Morphinans," *Tetrahedron Lett.* 44:6459-6462 (2003).
Zimmerman and Leander, "Opioid Antagonists: Structure Activity Relationships," *NIDA Res. Monogr.* 96:50-60 (1990).

*Primary Examiner*—Rita Desai
(74) *Attorney, Agent, or Firm*—Clark & Elbing LLP

(57) ABSTRACT

This invention features opioid compounds having activity at kappa and mu receptors, methods for preparing the mu/kappa opioids, and methods for the treatment of pain or a dopamine dysregulation disease, such as schizophrenia, attention deficit hyperactivity disorder (ADHD), attention deficit hyperactivity disorder (ADD), Parkinson's disease, hyperprolactinemia, depression, and addiction.

7 Claims, No Drawings

MIXED *KAPPA/MU* OPIOIDS AND USES THEREOF

CROSS-REFERENCE TO RELATED APPLICATIONS

The application claims benefit of U.S. Provisional Application Nos. 60/427,109 filed Nov. 18, 2002, and 60/461,157 filed Apr. 8, 2003, each of which is incorporated herein by reference.

STATEMENT AS TO FEDERALLY SPONSORED RESEARCH

This invention was sponsored in part by Grant #R01-DA014251 from the National Institutes of Health. The Government has certain rights to this invention.

BACKGROUND OF THE INVENTION

This invention relates to the field of therapeutics for the treatment of pain or a dopamine dysregulation disease, such as addiction.

Dopamine is one of the principal neurotransmitters in the central nervous system, where it is involved with motor function, perception, arousal, motivation and emotion. Abnormalities in dopaminergic neurotransmission have been implicated in various neurological and psychiatric disorders, including drug dependence. It has been found that addicting drugs such as nicotine, cocaine, amphetamine, methamphetamine, ethanol, heroin, and morphine enhance (in some cases directly, in other cases indirectly or even trans-synaptically) dopamine (DA) within the mesotelencephalic reward/reinforcement circuitry of the forebrain, presumably producing the enhanced brain reward that constitutes the drug user's "high." Alterations in the function of these DA systems have also been recovering addicts. For example, cocaine acts on these DA systems by binding to the dopamine transporter (DAT) and preventing DA reuptake into the presynaptic terminal and its indirect dopamine agonist effects are thought to be important for its addictive nature. Ritz et al., *Science* 237:1219 (1987).

There is a need for new therapeutic agents and methods for the treatment of dopamine dysregulation diseases. Such agents could be used, for example, to relieve a patient's craving for addictive drugs by changing the pharmacological actions of these drugs in the central nervous system.

SUMMARY OF THE INVENTION

We have discovered compounds which are active at mu and kappa opioid receptors. These mu/kappa opioids can be useful for the treatment of pain or a dopamine dysregulation disease, such as schizophrenia, attention deficit hyperactivity disorder (ADHD), attention deficit hyperactivity disorder (ADD), Parkinson's disease, hyperprolactinemia, depression, or addiction.

In a first aspect, the invention features a compound of formula I.

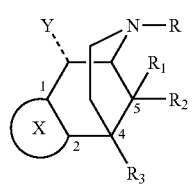
(I)

In formula I, X includes the carbon atoms at positions 1 and 2 and is described by one of formulas:

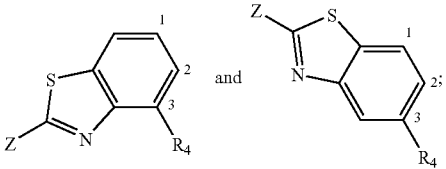

wherein Z is selected from —NHR$_5$ and —N(R$_6$)$_2$; R$_5$ is selected from H, C$_{1-7}$ alkyl, C$_{2-7}$ alkenyl, C$_{2-7}$ alkynyl, C$_{2-6}$ heterocyclyl, C$_{6-12}$ aryl, C$_{7-14}$ alkaryl, C$_{3-10}$ alkheterocyclyl, C$_{1-7}$ heteroalkyl, acyl, and fatty acid acyl; and each R$_6$ is, independently, selected from C$_{1-7}$ alkyl, C$_{2-7}$ alkenyl, C$_{2-7}$ alkynyl, C$_{2-6}$ heterocyclyl, C$_{6-12}$ aryl, C$_{7-14}$ alkaryl, C$_{3-10}$ alkheterocyclyl, and C$_{1-7}$ heteroalkyl.

Y, of formula I, is H, oxo, or methyl; R is selected from H, C$_{1-7}$ alkyl, C$_{2-7}$ alkenyl, C$_{2-7}$ alkynyl, C$_{2-6}$ heterocyclyl, C$_{6-12}$ aryl, C$_{7-14}$ alkaryl, C$_{3-10}$ alkheterocyclyl, and C$_{1-7}$ heteroalkyl; and R$_1$ is selected from H and CH$_3$. R$_4$ is H and R$_2$ and R$_3$ are each, independently, H, C$_{1-7}$ alkyl, or R$_2$ and R$_3$ combine to form a fused six-membered ring in which position 4 is connected to position 5 by one of formulas:

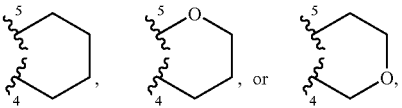

or R$_4$ combines with R$_2$ and R$_3$ to form a fused ring system in which position 3, 4, and 5 are connected by the formula:

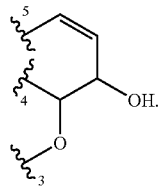

Compounds of formula I include those described by formulas Ia and Ib.

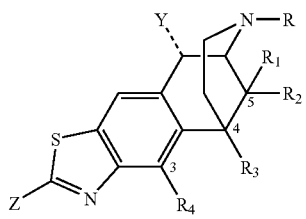
(Ia)

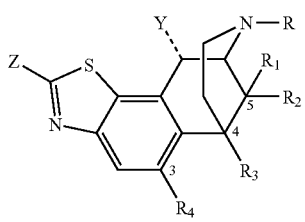
(Ib)

In formulas Ia and Ib, Y, R, $R_1$, $R_2$, $R_3$, $R_4$, and Z are defined as described above.

Desirably, compounds of formula I are further described by any one of formulas II-X.

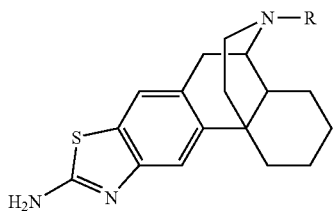
(II)

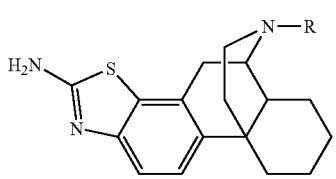
(III)

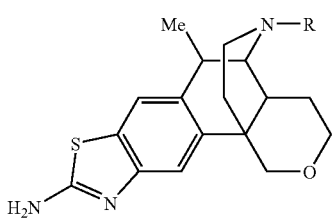
(IV)

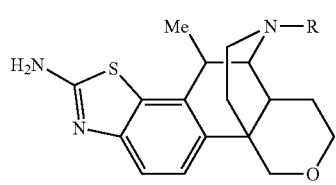
(V)

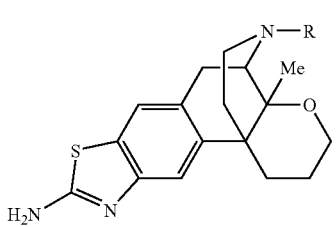
(VI)

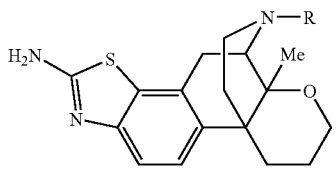
(VII)

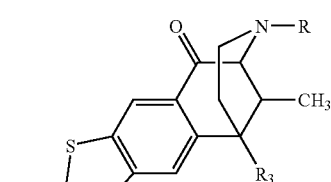
(VIII)

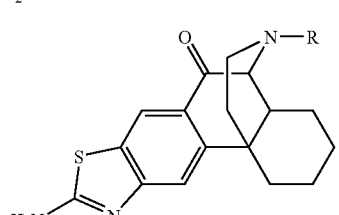
(IX)

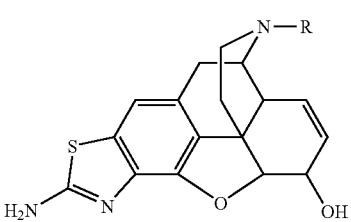
(X)

In formulas II-X, R is selected from H, $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl. In formula VIII, $R_3$ is $CH_3$ and $CH_2CH_3$.

For any of formulas I-X, R is desirably selected from the group consisting of $CH_3$, $CH_2$(cyclo-$C_4H_7$), $CH_2$(cyclo-$C_3H_5$), $CH(CH_3)$(cyclo-$C_3H_5$), $CH_2CH_2CH_2F$, $CH_2CH_2OCH_3$, $CH_2CH_2OCF_3$, $CH_2CH(CH_3)_2$, $CH_2CH=CH_2$, trans-$CH_2CH=CHI$, $CH_2C\equiv CH$, benzyl, phenethyl, 3,4-dichlorophenethyl, 3-furanylmethyl, 2-furanylmethyl, 3-tetrahydrofuranylmethyl, and 2-tetrahydrofuranylmethyl.

The invention also features compounds of formula XI.

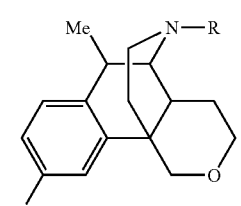
(XI)

In formula XI, R is selected from $CH_2CH_2CH_2F$, $CH_2CH_2OCH_3$, $CH_2CH_2OCF_3$, $CH_2CH(CH_3)_2$, trans-$CH_2CH=CHI$, $CH_2C\equiv CH$, benzyl, phenethyl, 3-furanylmethyl, 3-tetrahydrofuranylmethyl, and 3,4-dichlorophenethyl.

The invention also features compounds of formula XII.

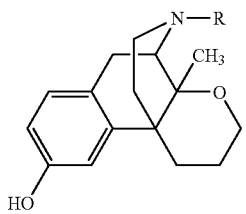

(XII)

In formula XII, R is selected from $CH_2CH_2CH_2F$, $CH_2CH_2OCH_3$, $CH_2CH_2OCF_3$, $CH_2CH(CH_3)_2$, trans-$CH_2CH=CHI$, benzyl, phenethyl, 3-furanylmethyl, 3-tetrahydrofuranylmethyl, and 3,4-dichlorophenethyl.

The invention also features compounds of formula XIII.

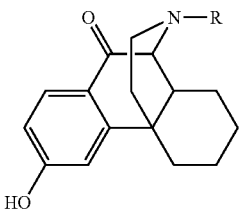

(XIII)

In formula XIII, R is selected from $CH_2(cyclo-C_4H_7)$, $CH_2CH_2CH_2F$, $CH_2CH_2OCH_3$, $CH_2CH_2OCF_3$, $CH_2CH(CH_3)_2$, $CH_2CH=CH_2$, trans-$CH_2CH=CHI$, $CH_2C\equiv CH$, benzyl, phenethyl, 3-furanylmethyl, 3-tetrahydrofuranylmethyl, and 3,4-dichlorophenethyl.

The invention also features compounds of formula XIV.

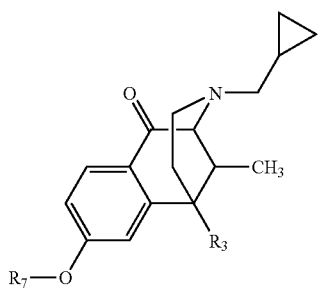

(XIV)

In formula XIV, $R_7$ is a fatty acid acyl and $R_3$ is selected from $CH_3$ and $CH_2CH_3$.

The invention features a method of treating a dopamine dysregulation disease. This method includes the step of administering to a patient in need thereof a composition having any of formulas I-XIV in an amount sufficient to treat the dopamine dysregulation disease. Dopamine dysregulation diseases that can be treated using the methods described herein include schizophrenia, attention deficit hyperactivity disorder (ADHD), attention deficit hyperactivity disorder (ADD), Parkinson's disease, hyperprolactinemia, depression, and addiction. Addictions that can be treated using the methods described herein include addictions to psychostimulants and narcotic analgesics. For example, the methods described herein can be used to treat addiction to cocaine.

The invention also features a method of treating pain in a patient in need thereof. This method includes the step of administering to the patient a composition having any of formulas I-XIV in an amount sufficient to treat the pain.

The invention features a pharmaceutical composition that includes a compound described by any one of formulas I-XIV in any pharmaceutically acceptable form, including isomers such as diastereomers and enantiomers, salts, solvates, and polymorphs thereof. The composition includes a compound of the invention along with a pharmaceutically acceptable carrier or diluent.

The invention also features a method of synthesizing a compound of formula I. The method includes the step of combining thiocyanate and bromine with a compound of formula XV.

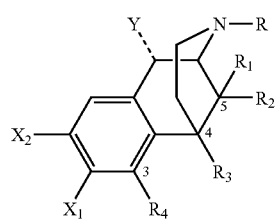

(XV)

In formula XV, Y is H, oxo, or methyl; R is selected from H, $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl; $R_1$ is selected from H and $CH_3$; and one of $X_1$ and $X_2$ is $NH_2$ and one of $X_1$ and $X_2$ is H. $R_4$ is H and $R_2$ and $R_3$ are each, independently, H, $C_{1-7}$ alkyl, or $R_2$ and $R_3$ combine to form a fused six-membered ring in which position 4 is connected to position 5 by one of formulas:

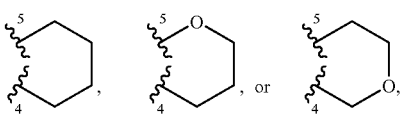

or $R_4$ combines with $R_2$ and $R_3$ to form a fused ring system in which position 3, 4, and 5 are connected by the formula:

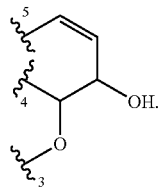

By "dopamine dysregulation disease" is meant a disease characterized or mediated by abnormal levels of dopamine in the brain. Examples of dopamine dysregulation diseases include schizophrenia, attention deficit hyperactivity disorder (ADHD), attention deficit hyperactivity disorder (ADD), Parkinson's disease, hyperprolactinemia, depression, Tourette's syndrome, and addiction.

As used herein, addiction refers to behavior resulting from compulsive substance use and is characterized by apparent total dependency on the substance. Symptomatic of the behavior is (i) overwhelming involvement with the use of the drug, (ii) the securing of its supply, and (iii) a high probability of relapse after withdrawal.

"Treating addiction" refers to administering a pharmaceutical composition for the purpose of preventing, reducing, or eliminating the self administration of an addictive drug by the patient.

Drugs of abuse include psychostimulants and narcotic analgesics. Examples of psychostimulants include, without limitation, amphetamine, dextroamphetamine, methamphetamine, phenmetrazine, diethylpropion, methylphenidate, cocaine and pharmaceutically acceptable salts thereof. Examples of narcotic analgesics include, without limitation, alfentanyl, alphaprodine, anileridine, bezitramide, codeine, dihydrocodeine, diphenoxylate, ethylmorphine, fentanyl, heroin, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan, thebaine and pharmaceutically acceptable salts thereof.

Compulsive drug use includes three independent components: tolerance, psychological dependence, and physical dependence. Tolerance produces a need to increase the dose of the drug after several administrations in order to achieve the same magnitude of effect. Physical dependence is an adaptive state produced by repeated drug administration and which manifests itself by intense physical disturbance when drug administration is halted. Psychological dependence is a condition characterized by an intense drive, craving or use for a drug whose effects the user feels are necessary for a sense of well being. See Feldman, R. S. and Quenzer, L. F. "Fundamentals of Neuropsychopharmocology" 418-422 (Sinaur Associates, Inc.) 1984 incorporated herein by reference as if set forth in full.

"Treating pain" refers to administering a pharmaceutical composition for the purpose of preventing, reducing, or eliminating pain in a patient in need thereof.

The term "administration" or "administering" refers to a method of giving a dosage of a pharmaceutical composition to a patient, where the method is, e.g., topical, transdermal, oral, intravenous, intraperitoneal, or intramuscular. The preferred method of administration can vary depending on various factors, e.g., the components of the pharmaceutical composition, site of administration, and severity of the pain or dopamine dysregulation disease.

In the generic descriptions of compounds of this invention, the number of atoms of a particular type in a substituent group is generally given as a range, e.g., an alkyl group containing from 1 to 7 carbon atoms or $C_{1-7}$ alkyl. Reference to such a range is intended to include specific references to groups having each of the integer number of atoms within the specified range. For example, an alkyl group from 1 to 7 carbon atoms includes each of $C_1$, $C_2$, $C_3$, $C_4$, $C_5$, $C_6$, and $C_7$. A $C_{1-7}$ heteroalkyl, for example, includes from 1 to 6 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups. The $C_{1-7}$ alkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, carboxyalkyl, and carboxyl groups. $C_{1-7}$ alkyls include, without limitation, methyl; ethyl; n-propyl; isopropyl; cyclopropyl; cyclopropylmethyl; cyclopropylethyl; n-butyl; iso-butyl; sec-butyl; tert-butyl; cyclobutyl; cyclobutylmethyl; cyclobutylethyl; n-pentyl; cyclopentyl; cyclopentylmethyl; cyclopentylethyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; and cyclohexyl.

By "$C_{2-7}$ alkenyl" is meant a branched or unbranched hydrocarbon group containing one or more double bonds and having from 2 to 7 carbon atoms. A $C_{2-7}$ alkenyl may optionally include monocyclic or polycyclic rings, in which each ring desirably has from three to six members. The $C_{2-7}$ alkenyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, carboxyalkyl, and carboxyl groups. $C_{2-7}$ alkenyls include, without limitation, vinyl; allyl; 2-cyclopropyl-1-ethenyl; 1-propenyl; 1-butenyl; 2-butenyl; 3-butenyl; 2-methyl-1-propenyl; 2-methyl-2-propenyl; 1-pentenyl; 2-pentenyl; 3-pentenyl; 4-pentenyl; 3-methyl-1-butenyl; 3-methyl-2-butenyl; 3-methyl-3-butenyl; 2-methyl-1-butenyl; 2-methyl-2-butenyl; 2-methyl-3-butenyl; 2-ethyl-2-propenyl; 1-methyl-1-butenyl; 1-methyl-2-butenyl; 1-methyl-3-butenyl; 2-methyl-2-pentenyl; 3-methyl-2-pentenyl; 4-methyl-2-pentenyl; 2-methyl-3-pentenyl; 3-methyl-3-pentenyl; 4-methyl-3-pentenyl; 2-methyl-4-pentenyl; 3-methyl-4-pentenyl; 1,2-dimethyl-1-propenyl; 1,2-dimethyl-1-butenyl; 1,3-dimethyl-1-butenyl; 1,2-dimethyl-2-butenyl; 1,1-dimethyl-2-butenyl; 2,3-dimethyl-2-butenyl; 2,3-dimethyl-3-butenyl; 1,3-dimethyl-3-butenyl; 1,1-dimethyl-3-butenyl and 2,2-dimethyl-3-butenyl.

By "$C_{2-7}$ alkynyl" is meant a branched or unbranched hydrocarbon group containing one or more triple bonds and having from 2 to 7 carbon atoms. A $C_{2-7}$ alkynyl may optionally include monocyclic, bicyclic, or tricyclic rings, in which each ring desirably has five or six members. The $C_{2-7}$ alkynyl group may be substituted or unsubstituted. Exemplary substituents include alkoxy, aryloxy, sulfhydryl, alkylthio, arylthio, halide, hydroxy, fluoroalkyl, perfluoroalkyl, amino, aminoalkyl, disubstituted amino, quaternary amino, hydroxyalkyl, carboxyalkyl, and carboxyl groups. $C_{2-7}$ alkynyls include, without limitation, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, 5-hexynyl; 1-methyl-2-propynyl; 1-methyl-2-butynyl; 1-methyl-3-butynyl; 2-methyl-3-butynyl; 1,2-dimethyl-3-butynyl; 2,2-dimethyl-3-butynyl; 1-methyl-2-pentynyl; 2-methyl-3-pentynyl; 1-methyl-4-pentynyl; 2-methyl-4-pentynyl; and 3-methyl-4-pentynyl.

By "$C_{2-6}$ heterocyclyl" is meant a stable 5- to 7-membered monocyclic or 7- to 14-membered bicyclic heterocyclic ring which is saturated partially unsaturated or unsaturated (aromatic), and which consists of 2 to 6 carbon atoms and 1, 2, 3 or 4 heteroatoms independently selected from the group consisting of N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoroalkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl,.oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary subsituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkheterocyclyl" is meant an alkyl substituted heterocyclic group having from 7 to 14 carbon atoms in addition to one or more heteroatoms (e.g., 3-furanylmethyl, 2-furanylmethyl, 3-tetrahydrofuranylmethyl, or 2-tetrahydrofuranylmethyl).

By "$C_{1-7}$ heteroalkyl" is meant a branched or unbranched alkyl, alkenyl, or alkynyl group having from 1 to 7 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, hydroxyalkyl, carboxyalkyl, and carboxyl groups.

By "acyl" is meant a chemical moiety with the formula R—C(O)—, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "halide" is meant bromine, chlorine, iodine, or fluorine.

By "fluoroalkyl" is meant an alkyl group that is substituted with a fluorine.

By "perfluoroalkyl" is meant an alkyl group consisting of only carbon and fluorine atoms.

By "carboxyalkyl" is meant a chemical moiety with the formula —(R)—COOH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ akaryl, $C_{3-10}$ alkheterocyclyl, or $C_{1-7}$ heteroalkyl.

By "hydroxyalkyl" is meant a chemical moiety with the formula —(R)—OH, wherein R is is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "alkoxy" is meant a chemical substituent of the formula —OR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "aryloxy" is meant a chemical substituent of the formula —OR, wherein R is a $C_{6-12}$ aryl group.

By "alkylthio" is meant a chemical substituent of the formula —SR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R")(R''')$^+$, wherein R, R', R", and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

By "fatty acid acyl" is meant a chemical moiety with the formula R—C(O)—, wherein R is a partially-saturated straight chain or branched hydrocarbon group having from 16 to 26 carbon atoms. Fatty acid acyls are derived from fatty acids including, without limitation, those occurring naturally in the brain. For example, fatty acids having 16 carbon atoms and 0, 1 or 2 double bonds (C16:0; C16:1 and C16:2), those with 18 carbon atoms and 1, 2 or 3 double bonds (C18:1; C18:2; and C18:3), those with 20 carbon atoms and 1, 2 or 4 double bonds (C20:1; C20:2; and C20:4) and those with 22 carbon atoms and 4, 5 or 6 double bonds (C22:4; C22:5 and C22:6). The fatty acids can be substituted or unsubstituted. Exemplary substituents include hydroxyl, halide, methyl, ethyl, propyl, isopropyl, butyl, and pentyl groups. Desirably, the fatty acid acyl is 4, 7, 10, 13, 16, 19 docosahexa-enoyl.

DETAILED DESCRIPTION

We have made compounds that are useful for the treatment of pain or dopamine dysregulation diseases, such as schizophrenia, attention deficit hyperactivity disorder (ADHD), attention deficit hyperactivity disorder (ADD), Parkinson's disease, hyperprolactinemia, depression, and addiction. The compounds are described by formulas I, XI, XII, XIII, and XIV. These compounds can be prepared as described in Examples 1-11, 16, and 19. Desirably, the compound is described by one of formulas II, III, IX, X, XVI, or XVII, wherein R is selected from $CH_2$(cyclo-$C_4H_7$), $CH_2$(cyclo-$C_3H_5$), $CH(CH_3)$(cyclo-$C_3H_5$), $CH_3$, and $CH_2CH=CH_2$.

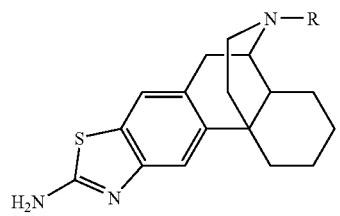

(II)

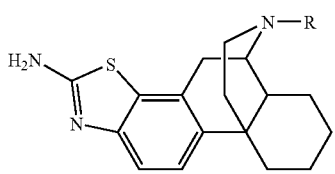

(III)

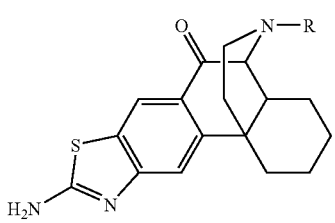

(IX)

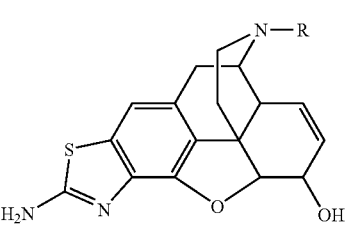

(X)

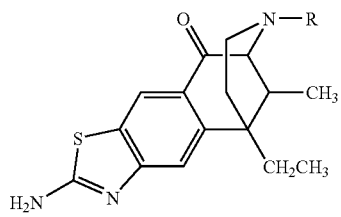

(XVI)

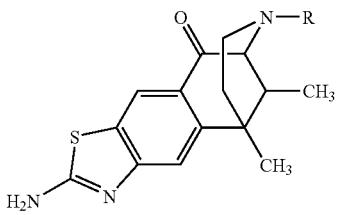

(XVII)

Assays

To determine their affinity for specific opioid receptors, compounds described herein can be characterized in radioligand receptor binding assays, using ligands that are specific for the mu, delta and kappa receptors. For example, the binding assays may utilize guinea pig brain membranes or stably transfected Chinese Hamster Ovary (CHO) cells expressing each of the three opioid receptors, as described in Example 12.

To determine their efficacy (e.g., agonist, partial agonist, antagonist) at a specific opioid receptor, compounds can be characterized by [$^{35}$S]GTPgammaS binding assay, as described in Example 13.

Compounds can be characterized in mouse antinociceptive tests to determine their in vivo pharmacological profile. For example, the warm-water tail flick test can be used to characterize the effects of compounds at the mu and delta opioid receptors. Most kappa agonists, such as U50,488, are not potent in thermal measurements of antinociception, but kappa agonists are very effective analgesics toward chemically-induced nociception. Therefore, the kappa effects of new compounds can be characterized in the acetic-acid writhing test. The antagonist effects of a compound can be determined by co-injecting either a mu-selective agonist (e.g., DAMGO), a delta-selective agonist (e.g., DPDPE), or a kappa-selective agonist (e.g., U50,488). The tail flick test can be used to measure antagonism at mu and delta receptors, and the writhing test can be used to measure antagonism at the kappa receptor.

Therapy

The mu/kappa opioids described herein can be used to modulate dopamine levels for the treatment of dopamine dysregulation diseases, such as schizophrenia, attention deficit hyperactivity disorder (ADHD), attention deficit hyperactivity disorder (ADD), Parkinson's disease, hyperprolactinemia, depression, and addiction. The mu/kappa opioids described herein are also useful for the treatment of pain.

The invention features a method of treating addiction by administering a compound having any of formulas I-XIV. The compounds disclosed herein may be administered by any appropriate route for treatment or prevention of a disease or condition associated with addiction. These may be administered with a pharmaceutically acceptable diluent, carrier, or excipient, in unit dosage form. Administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (20th ed., ed. A. R. Gennaro AR., 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycolate and deoxycholate, or may be oily solutions for administration in the form of nasal drops, or as a gel. The concentration of the compound in the formulation will vary depending upon a number of factors, including the dosage of the drug to be administered, and the route of administration.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include calcium, zinc, iron, and the like.

Administration of compounds in controlled release formulations is useful where the compound of formula I has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Pharmaceutical formulations of compounds of formulas I-XIV can include isomers such as diastereomers and enantiomers, mixtures of isomers, including racemic mixtures, salts, solvates, and polymorphs thereof.

The formulations can be administered to patients in therapeutically effective amounts. For example, an amount is administered which prevents, reduces, or eliminates the self administration of cocaine, or other addictive drugs. Typical dose ranges are from about 0.001 µg/kg to about 2 mg/kg of body weight per day. Desirably, a dose of between 0.001 µg/kg and 1 mg/kg of body weight, or 0.005 µg/kg and 0.5 mg/kg of body weight, is administered. The exemplary dosage of drug to be administered is likely to depend on such variables as the type and extent of the addiction, the overall health status of the particular patient, the formulation of the compound, and its route of administration. Standard clinical trials may be used to optimize the dose and dosing frequency for any particular compound.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLE 1

Synthesis of Morphinan and 10-keto-morphinan Derivatives.

Morphinan and 10-keto-morphinans can be prepared from commercially available levorphanol (Mallinckrodt) by the general procedure shown in Scheme 1 and described by Neumeyer, et al., *J. Med. Chem.* 43:114 (2000). O-methylation with trimethylsilyldiazomethane yields 5. Aoyama et al., *Chem. Pharm. Bull.* 32:3759 (1984). N-demethylation yields 6 which is O-demethylated followed by alkylation with an appropriate alkyl halide or acylation followed by reduction with lithium aluminum hydride to yield the morphinan derivative. 8 can be oxidized using $CrO_3$ as described by Michne et al., *J. Med. Chem.* 15:1278 (1972) and Neumeyer, et al., *J. Med. Chem.* 43:114 (2000). Further O-demethylation of the oxidation product yields 10-keto-morphinan derivatives.

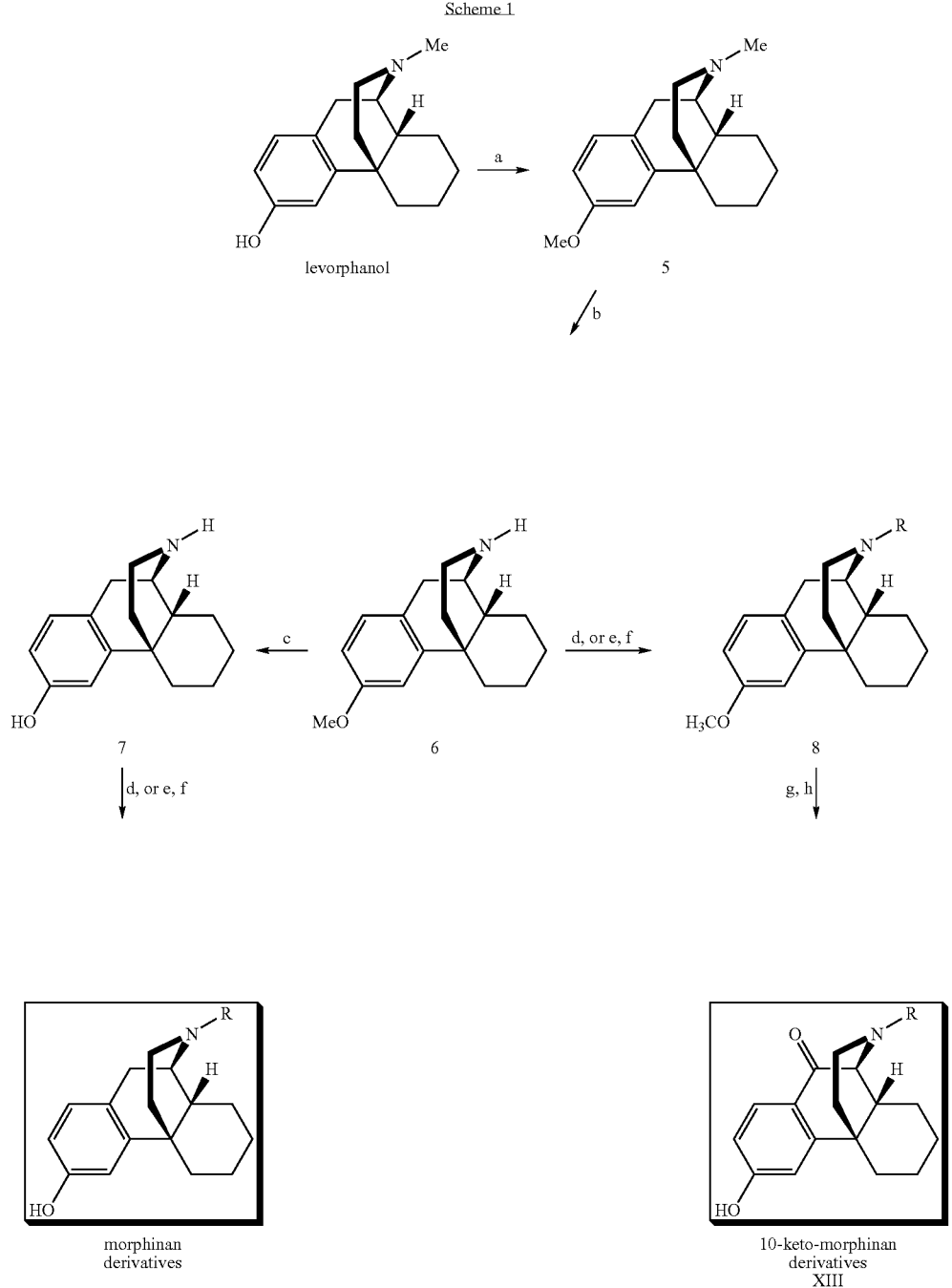
Reagents:
a). TMSCHN$_2$, Et$_3$N;
b). ClCO$_2$Et, then MeOH;
c). HBr, HOAc;
d). RX, NaHCO$_3$, DMF;
e). RCOCl, Et$_3$N;
f). LiAlH$_4$;
g). CrO$_3$, H$_2$SO$_4$;
h). BBr$_3$ or 48% HBr.

EXAMPLE 2
Synthesis of 10-methyl-6-oxamorphinan Derivatives.
10-methyl-6-oxamorphinan derivatives can be prepared by the general procedure shown in Scheme 2 and described by McElroy, et al., *J. Chem. Soc. Perkin. Trans.* 1:1563 (1990).
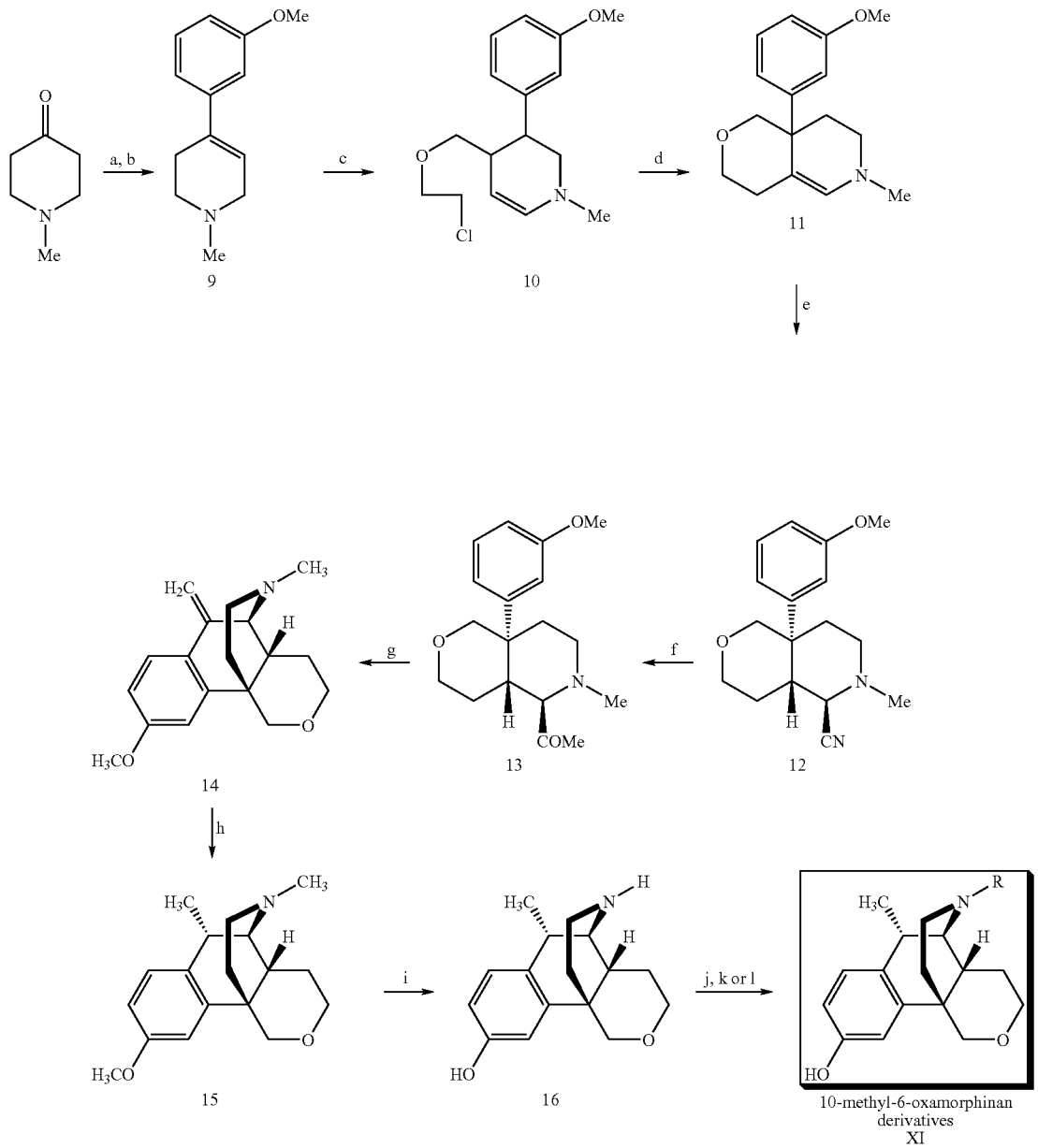
Reagents:
a). ArBr, BuLi;
b). H+;
c). BuLi, then ClCH$_2$OCH$_2$Cl;
d). NaI, MeCN;
e). KCN, pH 7.9;
f). MeLi;
g). BF$_3$•OEt$_2$;
h). H$_2$, Pd/C;
i). ClCO$_2$Et, then HBr, HOAc;
j). RCOCl;
k). LiAlH$_4$;
l). RX, NaHCO$_3$, DMF.

EXAMPLE 3

Synthesis of 8-oxamorphinan Derivatives.

14-methyl-8-oxamorphinan derivatives can be prepared by the general procedure shown in Scheme 3 and based on the procedure of Ahmed et al., *Can. J. Chem.* 53:3276 (1975). Alkylation of 7-methoxy-2-tetralone (Aldrich) with alkyl bromide yields 17, which is further alkylated with 2-chloro-N,N-dimethylethylamine to yield 18. Bromination of 18 yields 19 which is cyclized to form 20. Dequarternization of 20 yields 21. Addition of methylmagnesium iodide to 21 produces the alcohol 22 stereoselectively. Hydroboration-oxidation of 22 yields 23. Lambert et al., *J. Med. Chem.* 21:423 (1978). Mesylation followed by treatment with sodium hydride affords 25 which can be N and O demethylated to give 26. Further alkylation or acylation followed by reduction will yield 8-oxamorphinan derivatives of formula XII.

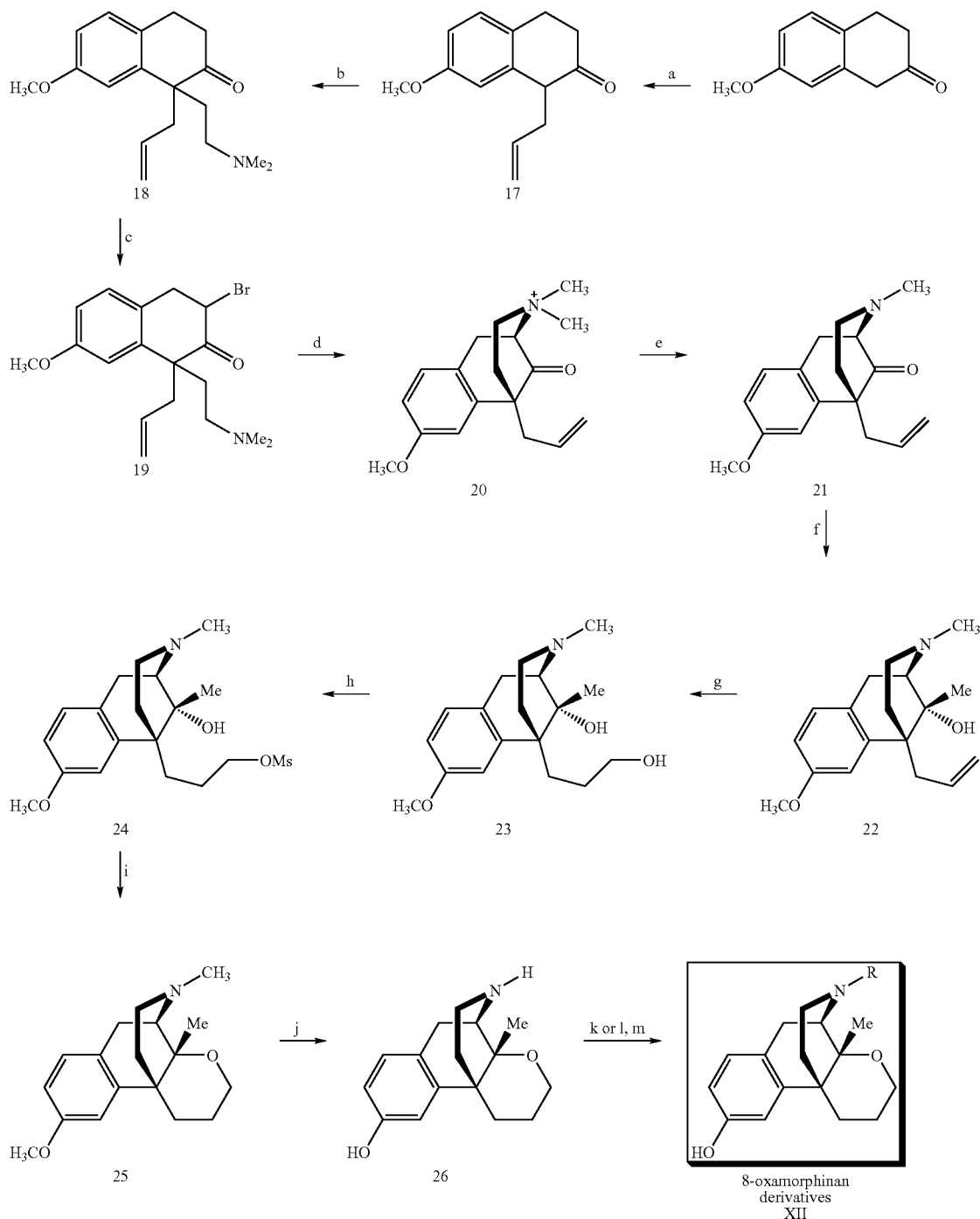

Scheme 3

-continued

Reagents:
a). allyl bromide, pyrrolidine;
b). ClCl$_2$CH2NMe$_2$, NaH;
c). pyrrolidone hydrotribromide;
d). NH4OH, then acetone;
e). 1-nonanol, heat;
f). MeMgI;
g). BH$_3$, THF, then H$_2$O$_2$, NaOH;
h). MsCl;
i). KOt-Bu, or NaH, DMF;
j). ClCO$_2$Et, then 48% HBr, HOAc;
k). RX, NaHCO$_3$;
l). RCOCl, Et$_3$N;
m). LiAlH$_4$.

EXAMPLE 4

Synthesis of Aminothiazole Morphinans of Formulas II and III.

Aminothiazole morphinan derivatives of formulas II and III can be synthesized by the general procedure shown in Scheme 4. Treatment of the appropriate morphinan derivative with triflic anhydride, or N-phenyl bis(trifluoromethanesulfonimide, yields the triflate 27, which can be converted to 28 by catalytic hydrogenation. Nitration of 28 with fuming nitric acid produces two isomers 29 and 30, which can be separated chromatographically. Reduction of 29 and 30 yield the corresponding amines 31 and 32, respectively. 2-aminothiazolemorphinan derivatives of formulas II and III can be obtained by treatment of 31 and 32 with KSCN and bromine in acetic acid. Maggiolo A. *J. Am. Chem.Soc.* 73:5815 (1951). The amine 31 can also be obtained by amination of the triflate using Buchwald's procedure followed by debenzylation by catalytic hydrogenation. Ahman and Buchwald, *Tetrahedron Lett.* 38:6363 (1997); Wolfe etal., *J. Org. Chem.* 65:1158(2000).

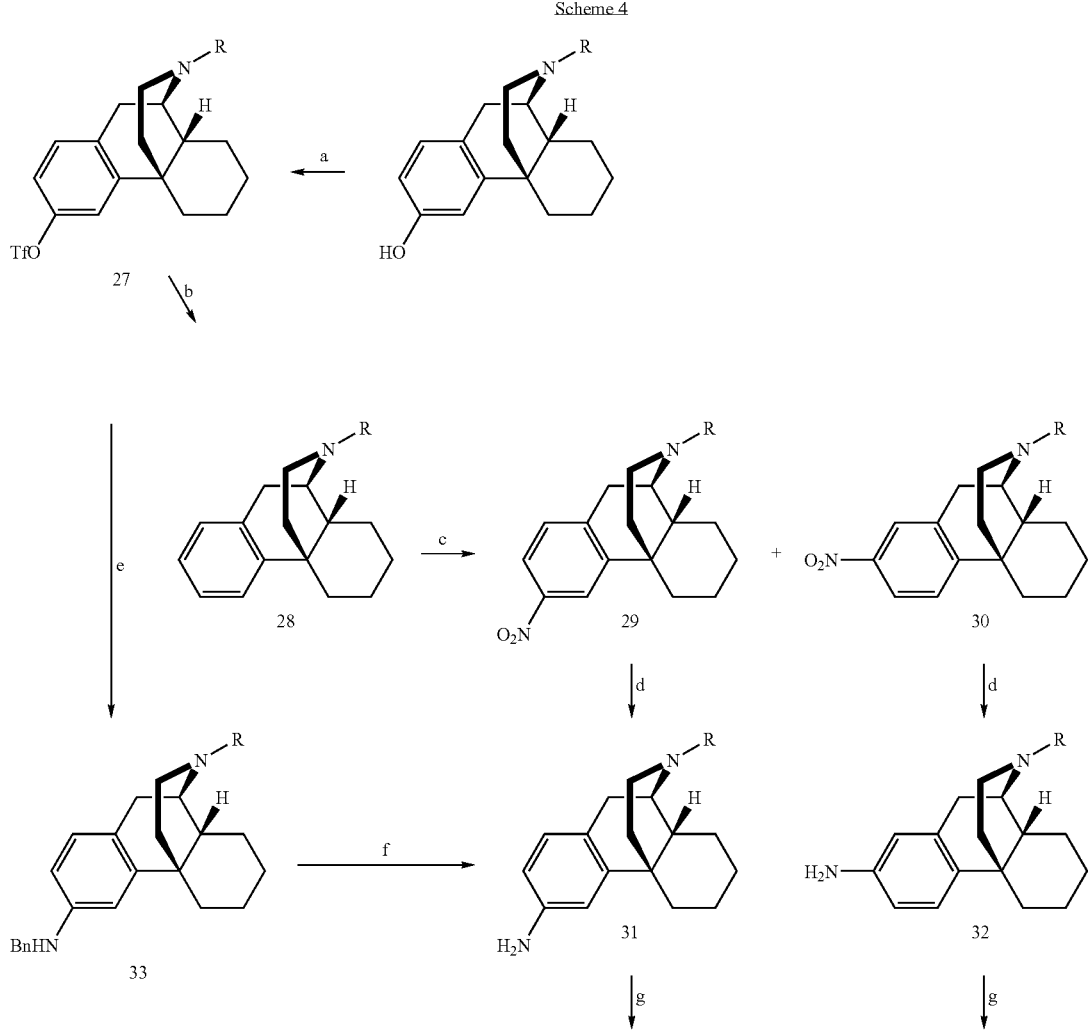

Scheme 4

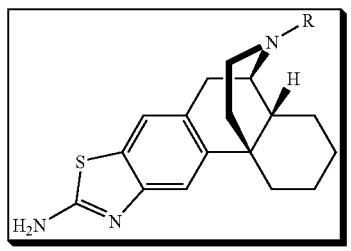

II

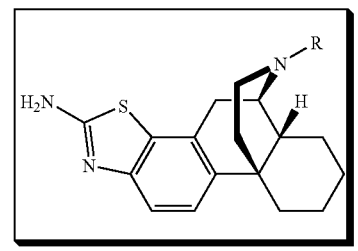

III

Reagents:
a). Tf$_2$O or PhNTf$_2$, Et$_3$N;
b). H$_2$, Pd/C;
c). HNO$_3$, HOAc;
d). H$_2$, Pd/C;
e). Pd(OAc)$_2$, BnNH$_2$, BINAP or (o-biphenyl)P(t-Bu)$_2$, Cs$_2$CO$_3$ or NaOt-Bu;
f). H$_2$, Pd/C;
g). KSCN, Br$_2$, HOAC.

EXAMPLE 5

Synthesis of Aminothiazole Benzomorphan Derivatives of Formula VIII.

Aminothiazole benzomorphan derivatives of formula VIII can be synthesized by the general procedure shown in Scheme 5. Quaternization of 3-methyl-4-ethylpyridine with methyl iodide followed by NaBH$_4$ reduction yields the tetrahydropyridine 35. Uwaydah et al., *J. Med. Chem.* 20:1374 (1977). Reaction of 35 with anisyl halide gave the tetrahydropyridinium salt 36. Stevens rearrangement can be effected by treating 36 with ethereal phenyllithium (Uwaydah, Id.) or powdered KOH (Yokoyama et al., *J. Med. Chem.* 13:488 (1970)) to afford the tetrahydropyridine 37. Subsequent cyclization of 37 in refluxing 48% HBr yields 38. The racemate 38 was resolved into its d and l antipodes 39 by fractional crystallization of the quinic acid salts. Tullar et al., *J. Med. Chem.* 10:383 (1967). O-Methylation of 39 with trimethylsilyldiazomethane yields 40. Aoyama, et al., *Chem. Pharm. Bull.* 32:3759 (1984). 40 can be oxidized using CrO$_3$ to give 41. N,O-Demethylation with chloroformate followed by acid hydrolysis yields 42, which can be alkylated with, for example, alkyl halide to give 43. Reaction of 43 with PhNTf$_2$ will yield the triflate 44, which can be aminated with benzophenone imine followed by hydrolysis to produce the amine 45. Wolfe et al., *Tetrahedron Lett.* 38:6367 (1997). 45 can be cyclized to the 2-aminothiazole benzomorphan of formula VIII by treatment with KSCN and bromine in acetic acid.

Scheme 5

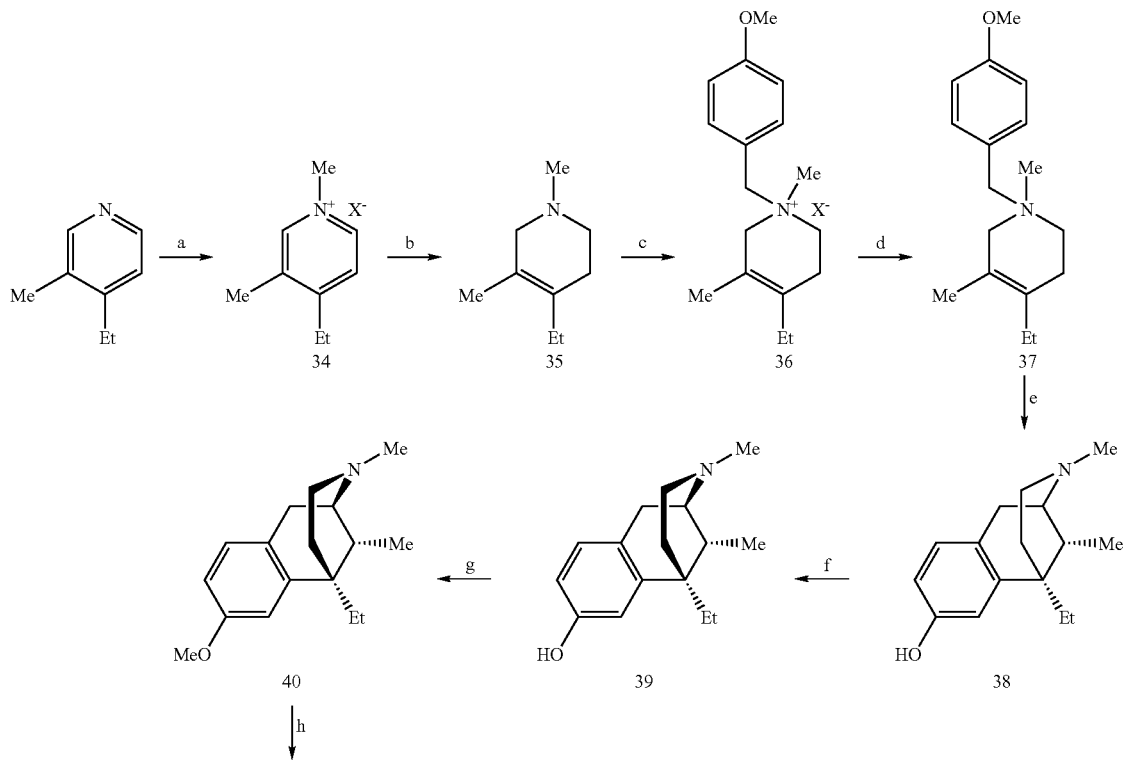

-continued
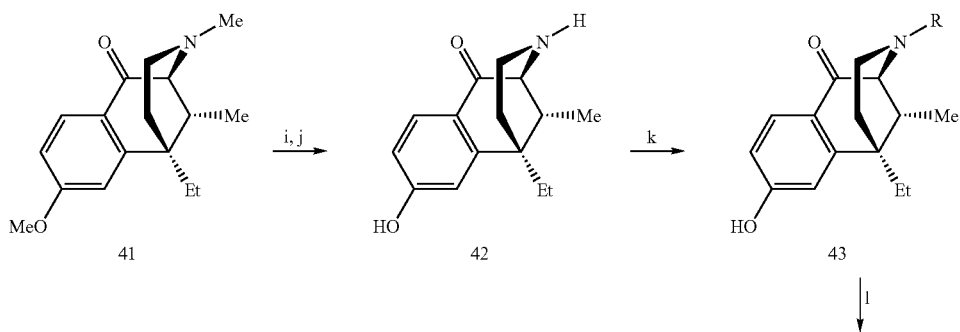
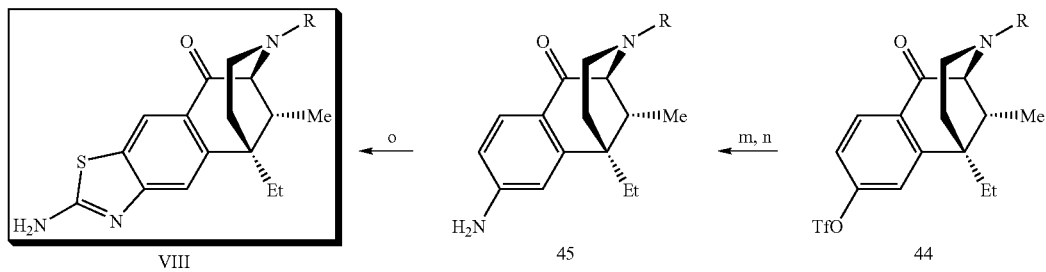
Reagents:
a). MeI;
b). NaBH₄, NaOH, MeOH—H₂O;
c). ArCH₂X;
d). PhLi/Et₂O or powdered KOH;
e). 48% HBr;
f). resolution with quinic acid;
g). TMSCHN₂;
h). CrO₃, H₂SO₄;
i). ClCO₂Et;
j). 48% HBr, HOAc;
k). RX, NaHCO₃;
l). PhN(Tf)₂, Et₃N;
m). benzophenone imine, Pd(OAc)₂, BINAP, Cs₂CO₃;
n). cat. HCl, wet THF;
o). KSCN, Br₂, HOAc.

EXAMPLE 6

Synthesis of Aminothiazole 10-keto-morphinans of Formula IX.

Aminothiazole 10-keto-morphinan derivatives of formula IX can be synthesized by the general procedure shown in Scheme 6. Reaction of 10-keto-morphinans with PhNTf$_2$ will yield the triflate 46, which can be aminated with benzophenone imine followed by hydrolysis to produce the amine 47 as described in Example 5. 47 can be cyclized to the 2-aminothiazole 10-keto-morphinan of formula IX by treatment with KSCN and bromine in acetic acid.

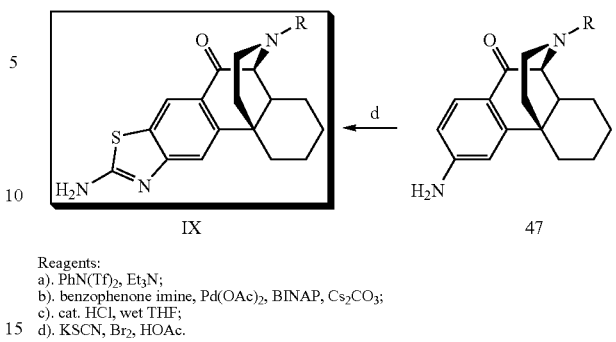

Reagents:
a). PhN(Tf)$_2$, Et$_3$N;
b). benzophenone imine, Pd(OAc)$_2$, BINAP, Cs$_2$CO$_3$;
c). cat. HCl, wet THF;
d). KSCN, Br$_2$, HOAc.

EXAMPLE 7

Synthesis of Aminothiazole 6-oxamorphinans of Formula IV and V.

Aminothiazole 6-oxamorphinan derivatives of formulas IV and V can be synthesized by the general procedure shown in Scheme 7 and Example 4.

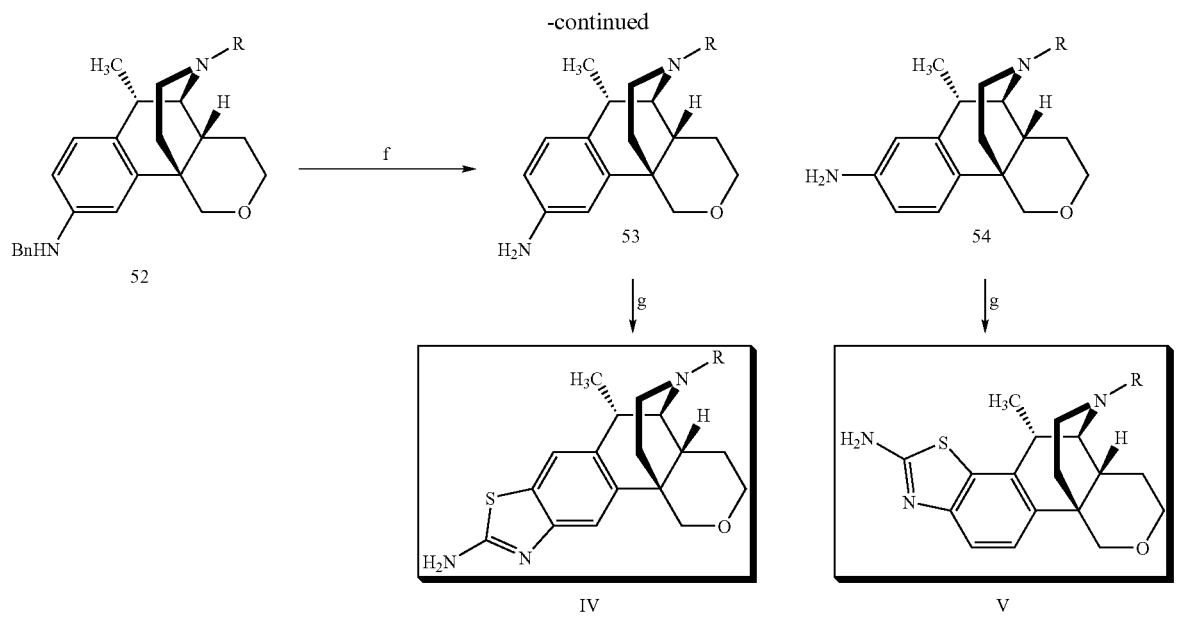
Reagents:
a). Tf₂O, Et₃N;
b). H₂, Pd/C;
c). HNO₃, HOAc;
d). H₂, Pd/C;
e). Pd(OAc)₂, BnNH₂, BINAP or (o-biphenyl)P(t-Bu)₂, Cs₂CO₃ or NaOt-Bu;
f). H₂, Pd/C;
g). KSCN, Br₂, HOAC.
EXAMPLE 8
Synthesis of Aminothiazole 8-oxamorphinans of Formula VI and VII.
Aminothiazole 8-oxamorphinan derivatives of formulas VI and VII can be synthesized by the general procedure shown in Scheme 8 and Example 4.
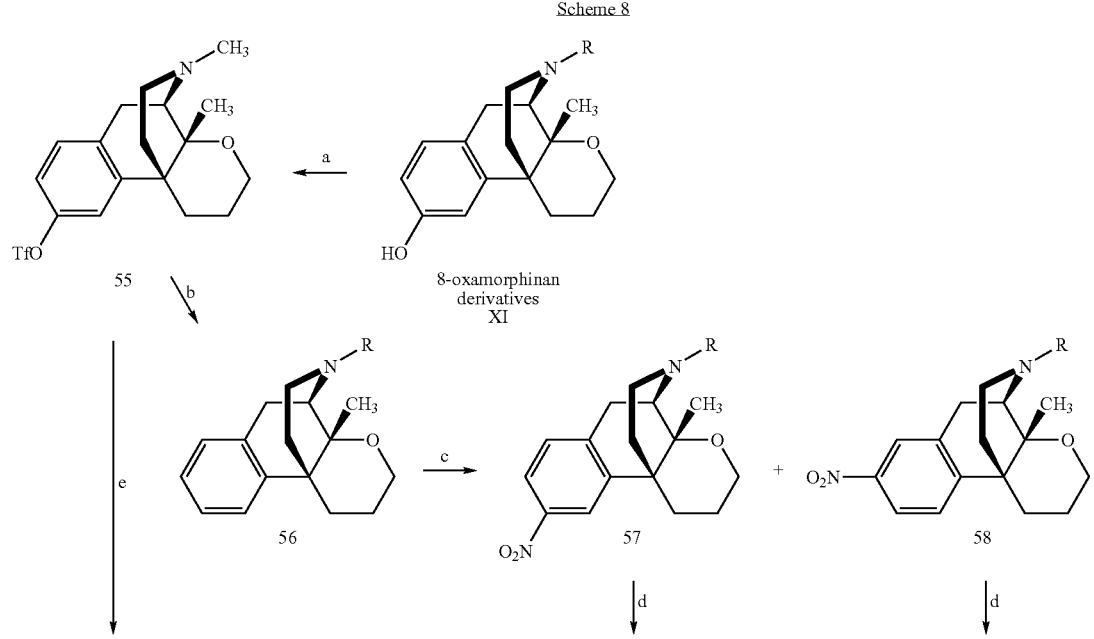

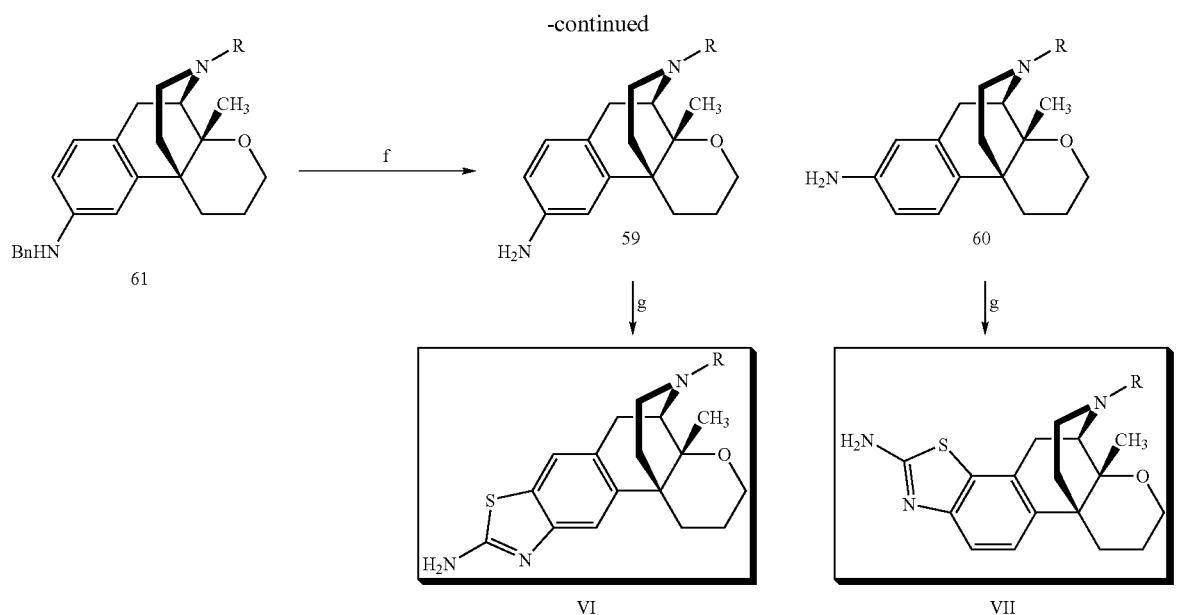

Reagents:
a). Tf₂O, Et₃N;
b). H₂, Pd/C;
c). HNO₃, HOAc;
d). H₂, Pd/C;
e). Pd(OAc)₂, BnNH₂, BINAP or (o-biphenyl)P(t-Bu)₂, Cs₂CO₃ or NaOt-Bu;
f). H₂, Pd/C;
g). KSCN, Br₂, HOAC.

EXAMPLE 9

Synthesis of Aminothiazoles of Formula X.

Aminothiazoles of formula X can be prepared using the general procedure of Scheme 9, starting from normorphine. N-alkylation of normorphine with an alkyl bromide yields the N-alkylmorphine 61, which can be selectively triflated to yield compound 62 using known methods (see, for example, Zhang, A., Neumeyer, J. L. *Org. Lett.*, 5, 201 (2003). This is followed by treatment with tetrabutyldimethylsilyl chloride (TBDMSCl) and imidazole to yield the 6-hydroxy protected analog 63. The Pd-catalyzed amination of 63 can be carried out using the method described by Wolfe, J. P.; Ahman, J.; Sdighi, J. P.; Singer, R. A.; Buchwald, S. L. *Tetrahedron Lett.*, 38, 6367 (1997) to afford 64. Compound 64 is treated with KSCN and bromine in HOAc to form the aminothiazole (Vliet, L. A.; Rodenhuis, N; Wikström, H. *J. Med. Chem.* 43, 3549 (2000). Subsequent deprotection of the 6 OH group with tetrabutylammonium fluoride (TBAF) in THF yields the target compound of formula X.

Scheme 9

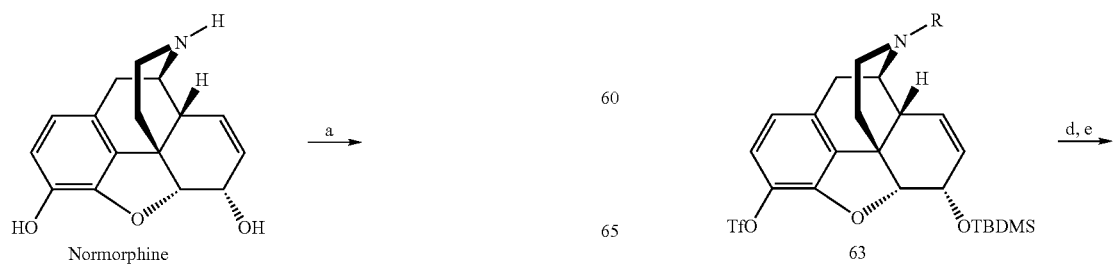

33

-continued

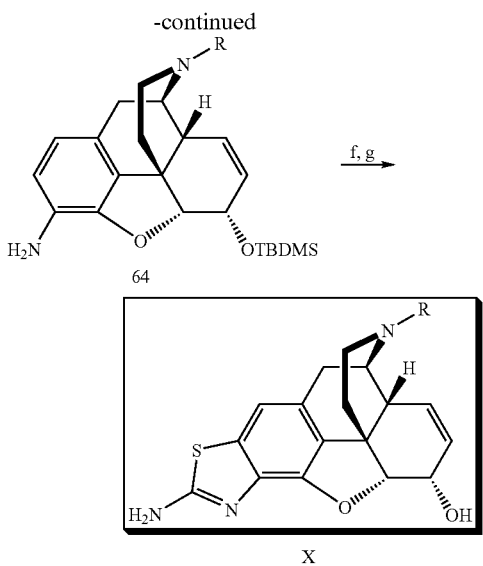

Reagents:
a) RX, NaHCO₃, DMF;
b) Tf₂NPh, Et₃N, CH₂Cl₂;
c) TBDMSCl, imidazole, THF;
d) benzophenone imine, Pd(OAc)₂, BINAP, Cs₂CO₃, THF;
e) NH₂OH•HCl, NaOAc, MeOH;
f) KSCN, Br₂, HOAc;
g) TBAF, THF.

EXAMPLE 10

Synthesis of Acyl and Alkyl Derivatives of Aminothiazole Compounds of Formulas II-IX.

Acyl-aminothiazole compounds can be synthesized by reaction of a compound of formulas II-IX with an acid halide. Alkyl-aminothiazole compounds can be synthesized by condensation of an aldehyde or ketone with a compound of formulas II-IX followed by reduction with cyanoborohydride. Numerous techniques for the acylation and alkylation of the amines are known in the art. See, for example, J. March, Advanced Organic Chemistry: Reactions, Mechanisms and Structure, John Wiley & Sons, Inc. 1992.

EXAMPLE 11

Synthesis of Benzomorphan Esters of Formula XIV.

As shown in Scheme 10, acylation of 65 with docosahexaenoyl chloride yields the fatty acid ester XIV.

Scheme 10

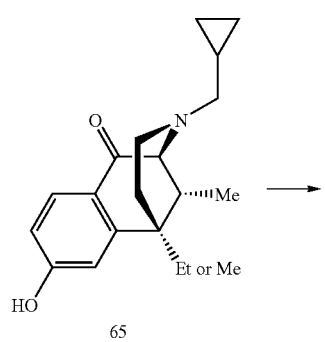

34

-continued

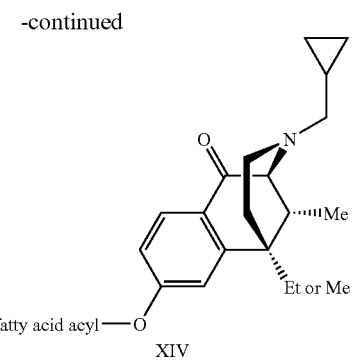

EXAMPLE 12

Radioligand Binding Assays.

Compounds can be characterized in radioligand receptor binding assays, using ligands that are specific for the mu, delta and kappa receptors. The binding assays may utilize guinea pig brain membranes or stably transfected Chinese Hamster Ovary (CHO) cells expressing each of the three opioid receptors. Membranes can be isolated from CHO cells that stably express either the human mu, delta or kappa opioid receptors. At approximately 80% confluence, the cells are harvested by the use of a cell scraper. The cells and media from the plates are centrifuged at 200×g for 10 mm at 4° C.; resuspended in 50 mM Tris-HCl, pH 7.5; homogenized by the use of a Polytron; centrifuged at 48,000×g for 20 mm at 4° C.; and resuspended in 50 mM Tris-HCl, pH 7.5, at a protein concentration of 5-10 mg/ml, as determined by the Bradford method. The membranes are stored frozen, at −80° C. until use.

Cell membranes are incubated at 25° C. with the radiolabeled ligands in a final volume of 1 ml of 50 mM Tris-HCl, pH 7.5. Incubation times of 60 minutes are used for the mu-selective peptide [³H]DAMGO and the kappa-selective ligand [³H]U69,593, and 4 hours of incubation for the delta-selective antagonist [³H]naltrindole. Nonspecific binding is measured by inclusion of 1 μM naloxone. The binding can be terminated by filtering the samples through Schleicher & Scheull No. 32 glass fiber filters using a Brandel 48-well cell harvester. The filters are subsequently washed three times with 3 ml of cold 50 mM Tris-HCl, pH 7.5, and can be counted in 2 ml of Ecoscint A scintillation fluid. For [³H]U69,593 binding, the filters are soaked in 0.1% polyethylenimine for at least 30 minutes before use. IC₅₀ values can be calculated by a least squares fit to a logarithm-probit analysis. $K_i$ values of unlabeled compounds are calculated from the equation $K_i = (IC_{50})/1+S$ where S=(concentration of radioligand) ($K_d$ of radioligand). Cheng and Prusoff, *Biochem. Pharmacol.* 22:3099 (1973). Alternatively, guinea pig brain membranes can be prepared and used as previously described in Neumeyer, et al., *J. Med. Chem.* 43:114 (2000).

EXAMPLE 13

[³⁵S]GTPgammaS Binding Assays.

Membranes from the CHO cell lines, expressing either the mu, delta or kappa receptor, are incubated with 12 concen trations of each opioid for 60 minutes at 30° C. in a final volume of 0.5 ml of assay buffer (50 mM Tris-HCl, 3 mM MgCl$_2$, 0.2 mM EGTA, 100 mM NaCl, pH 7.5) containing 3 μM GDP and 0.08 nM [$^{35}$S]GTPgammaS. Basal binding can be determined in the presence of GDP and the absence of opioids, and nonspecific binding can be determined by including 10 μM unlabeled [$^{35}$S]GTPgammaS. The incubation can be terminated by filtration under vacuum through glass fiber filters, followed by three washes with 3 ml ice-cold 50 mM Tris-HCl, pH 7.5. Samples can be allowed to equilibrate overnight and can be counted in 2 ml Ecoscint A scintillation fluid for 2 minutes in a liquid scintillation counter.

For [$^{35}$S]GTPgammaS binding assays, percent stimulation of [$^{35}$S]GTPgammaS binding is defined as [(opioid-stimulated binding-basal binding) basal binding]×100. Percent stimulation is plotted as a function of opioid concentration (log scale), and EC$_{50}$ and Emax values are determined by linear regression analysis. All data is compared across conditions using ANOVA and non-paired two-tailed Student's tests.

EXAMPLE 14

Tail Flick Assay.

The thermal nociceptive stimulus can be 55° C. water with the latency to tail flick or withdrawal taken as the endpoint. McLaughlin et al., *J. Pharmacol. Exp. Ther.* 289:304 (1999); McLaughlin et al., *Eur. J. Pharmacol.* 320:121 (1997); Neumeyer, et al., *J. Med. Chem.* 43:114 (2000); and Xu et al., *J. Pharmacol. Exp. Ther.* 279:539 (1996). Intracerebroventricular injections are made directly into the lateral ventricle. The mouse is lightly anesthetized with ether, an incision is made in the scalp, and the injection is made 2 mm lateral and 2 mm caudal to bregma at a depth of 3 mm using a 10 μl Hamilton microliter syringe. The volume of all i.c.v. injections are 5 μl. After determining control latencies, the mice receives graded i.c.v. doses of opioid agonists or antagonists at various times. When measuring agonist activity, the selective antagonists, β-FNA (mu), ICI 174,864 (delta) and nor-BNI (kappa) can be used as previously described. McLaughlin et al., *J. Pharmacol. Exp. Ther.* 289:304 (1999). When measuring antagonist activity, morphine, DPDPE, and U50,488 are co-administered with the new compounds as a single i.c.v. injection with testing taking place 20 mm after the injection. A cut-off time of 15 seconds is used; if the mouse fails to display a tail flick, the tail is removed from the water and that animal can be assigned a maximal antinociceptive score of 100%. Mice showing no response within 5 seconds in the initial control test are eliminated from the experiment. Antinociception at each time point can be calculated according to the following formula: % antinociception=100×(test latency−control latency)/(15−control latency).

Antagonist activity can be determined by calculating the pA$_2$ values for a compound. For example, a morphine dose-response curve is generated. Then morphine and the putative antagonist is co-injected and the morphine dose-response curve is generated in the presence of varying doses of the antagonist. The tail flick test can be used to characterize both mu and delta agonist and antagonist activity.

EXAMPLE 15

Writhing Assay.

Because antinociception induced by kappa opioid agonists has been difficult to evaluate in the tail flick test, the action of the compounds can be determined in the mouse acetic-acid writhing test. After receiving i.c.v. doses of opioid agonists and antagonists at various times, an i.p. injection of 0.6% acetic acid (10 ml/kg) are administered to each mouse. Five minutes after administration, the number of writhing signs displayed by each mouse are counted for an additional 5 minutes. Antinociception for each tested mouse can be calculated by comparing the test group to a control group in which mice were treated with i.c.v. vehicle solution.

EXAMPLE 16

Aminothiazole Derivatives of Levorphanol.

Using a method analogous to that described in Example 4, aminothiazole derivatives were prepared from commercially available Levorphanol (R═CH$_3$). Levorphanol was treated with N-phenyl bis(trifluoromethanesulfonimide) and triethylamine to yield the triflate (Scheme 4, compound 27 where R═CH$_3$) in 85% yield. Reduction of the triflate (Scheme 4, step b) using Pd/C (10%) as a catalyst and ammonium formate as a proton source gave N-methylmorphinan in almost quantitative yield. Nitration (Scheme 4, step c) was performed using HNO$_3$/H$_2$SO$_4$ in nitromethane to produce an oil containing a 1:1 mixture of two isomers, 2-nitro-N-methylmorphinan and 3-nitro-N-methylmorphinan. After conversion to the corresponding dibenzyl-D-tartate salt, repeated crystallizations from EtOH/H$_2$O (100/40) gave pure compound 67 in 22% yield. The mother liquor was repeatedly evaporated, and the residue repeatedly recrystallized from $^i$PrOH/H$_2$O (2/1) until GC analysis indicated it was pure compound 68 (10% yield).

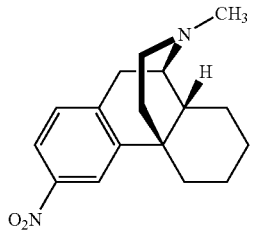

67

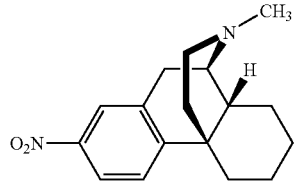

68

Compounds 67 and 68 were reduced to their corresponding amines using Pd/C (10%) and ammonium formate in methanol in 85% and 80% yields, respectively. The resulting amines were treated with potassium thiocyanate and bromine in acetic acid. The corresponding aminothiazoles 69 and 70 were formed in 68% and 60% yields, respectively.

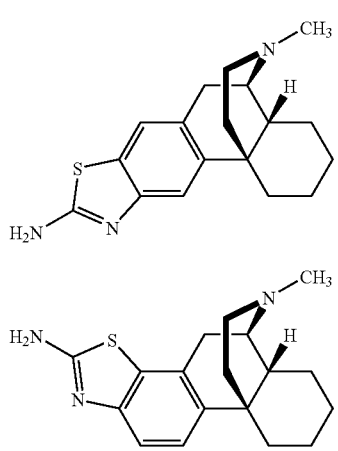

69

70

Data for compounds 67-70 follow. For 2-nitro-N-methylmorphinan 68 (hydrochloride): MS m/z 287 (M$^+$–Cl); $^1$H NMR (CD$_3$OD, 300 MHz) δ: 8.14 (d, J=9.1 Hz, 1H), 8.12 (s, 1H), 7.66 (d, J=8.5 Hz, 1H), 3.31 (m, 4H), 2.96 (s, 3H), 2.62 (d, J=13.8 Hz, 2H), 2.18 (m, 1H), 2.08 (m, 1H), 2.08 (m, 1H), 1.60 (m, 6H) 1.10 (m, 2H). Anal. Calcd. for C$_{17}$H$_{23}$N$_2$O$_2$Cl: C, 63.25; H, 7.18; N, 8.68. Found: C, 63.12; H, 7.21; N, 8.68. For 3-nitro-N-methylmorphinan 67 (hydrochloride): MS m/z 287 (M$^+$–Cl); $^1$H NMR (CD$_3$OD, 300 MHz) δ: 8.25 (s, 1H), 8.11 (d, J=8.4 Hz, 1H), 7.52 (d, J=8.4 Hz, 1H), 3.30 (m, 4H), 2.94 (s, 3H), 2.61 (d, J=13.4 Hz, 2H), 2.17 (d, J=12.5 Hz, 1H), 2.02 (m, 1H), 1.63 (m, 6H), 1.23 (m, 1H), 1.07 (m, 1H). Anal. Calcd. for C$_{17}$H$_{23}$N$_2$O$_2$Cl: C, 63.25; H, 7.18; N, 8.68. Found: C, 63.24; H, 7.18; N, 8.60. For aminothiazole 70: pale yellow foam. MS m/z 314 (M$^+$+1); $^1$H NMR (CD$_3$OD, 300 MHz) δ: 7.25 and 7.18 (Abq, J=19.5 Hz, both d with 8.7 and 8.1 Hz, respectively, 2H), 4.87 (brs, 2H), 3.30 (m, 1H), 2.87 (m, 2H), 2.62 (m, 1H), 2.41 (m, 1H), 2.36 (s, 3H), 2.01 (m, 1H), 1.73 (m, 3H), 1.34 (m, 7H); $^{13}$C NMR (CDCl$_3$, 75 MHz) δ: 169.2, 150.6, 134.2, 131.1, 130.0, 124.3, 117.3, 59.1, 48.1, 46.3, 42.8, 42.7, 37.7, 27.7, 27.6, 25.2, 23.2. Anal. Calcd. for C$_{18}$H$_{23}$N$_3$S-0.5H$_2$O: C, 67.04; H, 7.50; N, 13.03. Found: C, 66.99; H, 7.33; N, 12.70. For aminothiazole 69: pale yellow foam. MS m/z 314 (M$^+$+1); $^1$H NMR (CD$_3$OD, 300 MHz) δ: 7.36 (s, 1H), 7.31 (s, 1H), 4.20 (brs, 2H), 3.09 (d, J=18.0 Hz, 1H), 2.81 (m, 2H), 2.44 (m, 1H), 2.39 (m, 3H), 2.12 (m, 1H), 1.75 (m, 3H), 1.42 (m, 8H); $^{13}$C NMR (CDCl$_3$, 75 MHz) δ: 169.2, 150.6, 134.2, 131.1, 130.0, 124.3, 117.3, 59.1, 48.0, 46.3, 42.8, 42.7, 37.7, 27.7, 27.6, 25.2, 23.2. Anal. Calcd. for C$_{18}$H$_{23}$N$_3$S-0.5H$_2$O: C, 67.04; H, 7.50; N, 13.03. Found: C, 67.43; H, 7.30; N, 12.79.

Aminothiazole derivatives in which R is —CH$_2$(cyclo-C$_3$H$_5$) and —CH$_2$(cyclo-C$_4$H$_7$) can be prepared in a similar fashion.

EXAMPLE 17

K$_i$ Values for μ, δ, and κ Binding of Aminothiazoles to CHO Membranes.

Four aminothiazole compounds, compounds 69-72 below, were prepared using the methods described herein and their affinity and selectivity at the three opioid receptors were evaluated. As described in Example 12, 0.5 milligrams of protein per sample was incubated with 12 different concentrations of the compounds in the presence of receptor-specific radioligands at 25° C. in a final volume of 1 mL (50 mM Tris-HCl buffer, pH 7.5). Nonspecific binding was determined using 10 μM naloxone. The data in Table 1 are the mean values SEM from three experiments performed in triplicate.

TABLE 1

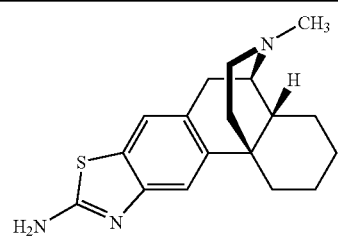

69

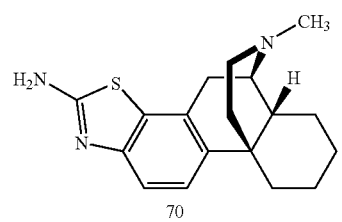

70

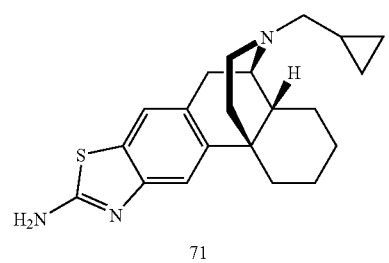

71

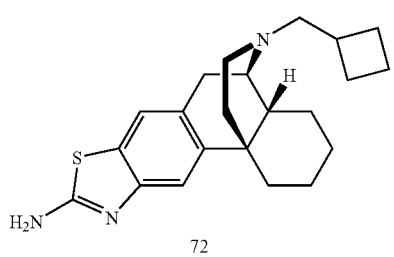

72

| Com- pound | [$^3$H]DAMGO (μ) | [$^3$H]Naltrindole (δ) | [$^3$H]U69,593 (κ) | Selectivity μ:κ | δ:κ |
|---|---|---|---|---|---|
| 69 | 130 ± 5.8" | 1100 ± 30 | 29 ± 1.4 | 4.5 | 38 |
| 70 | 1.10 ± 0.13 | 190 ± 9.7 | 6.4 ± 0.53 | 0.17 | 30 |
| 71 | 1.5 ± 0.21 | 29 ± 2.0 | 0.049 ± 0.0046 | 30 | 590 |
| 72 | 7.10 ± 0.47 | 230 ± 21 | 0.79 ± 0.02 | 9.0 | 290 |

EXAMPLE 18

[$^{35}$S]GTPγS Binding Studies with Aminothiazole Compounds.

To determine their efficacy (e.g., agonist, partial agonist, antagonist) at a specific opioid receptor, compounds 71 and 72 were characterized by [$^{35}$S]GTPgammaS binding assay, as described in Example 13. Compound 71 is a κ and μ agonist. It is more potent at κ than at μ. Compound 72 is a κ agonist with a weak agonist and antagonist activity at the μ receptor.

EXAMPLE 19

Synthesis of 10-ketomorphinans.

10-ketomorphinans were prepared as follows. First, 3-hydroxy-10-keto-normorphinan, prepared as described by Neumeyer et al., *J. Med. Chem.*, 43:114 (2000), (300 mg, 1.16 mmol) was combined with 1.2 equivalents of alkyl bromide, e.g., propargyl bromide or cyclobutylmethyl bromide, and NaHCO$_3$ (117 mg, 1.4 mmol) in dry DMF (15 mL). The mixture was heated under nitrogen at 75° C. for 24 hours. The solvent was removed under reduced pressure. The remaining material was taken up with CHCl$_3$ (50 mL), washed with water (2×25 mL), dried (Na$_2$SO$_4$), and concentrated. The residue was purified by flash chromatography (hexane/EtOAc: 4/1) to yield compounds 73 and 74.

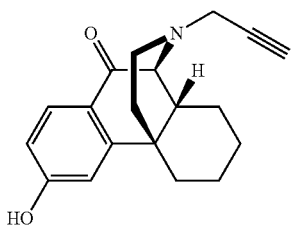
73

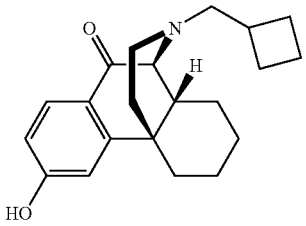
74

In a second approach, 3-hydroxy-10-keto-normorphinan (300 mg, 1.16 mmol) in 10 mL of anhydrous EtOH, was added a solution of Et$_3$N (1.2 equiv.), followed by alkyl bromide (1.2 equiv.). The resulting mixture was heated under nitrogen at 75° C. for 48 hours. The solvent was removed under reduced pressure and the remaining material was taken up in CHCl$_3$ (50 mL), washed with brine (2×25 mL), dried (Na2SO4), and concentrated. The residue was further purified by flash chromatography (hexane/EtOAc: 4/1) to yield compounds 75, 76, and 77.

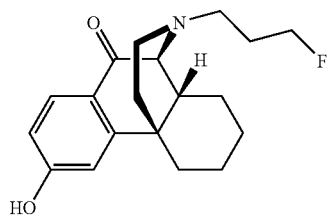
75

-continued

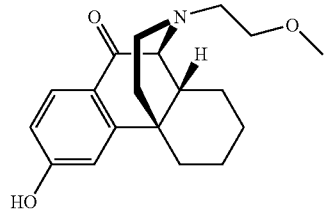
76

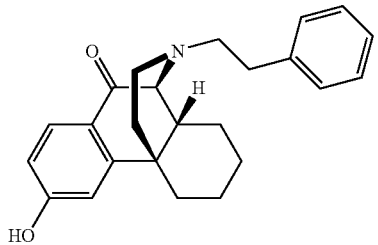
77

Data for compounds 73-77 follow. For 3-Hydroxy-10-keto-N-propargylmorphinan 73: Pale-yellow solid (43%). Mp: 221-223° C. (Dec.). MS: m/e 295 (M+); $^1$H NMR (CDCl$_3$, 300 MHz): δ 7.98 (dd, J=1.8, 8.4 Hz, 1H), 6.79 (m, 2H), 3.42 (dt, J=2.4, 16.5 Hz, 1H), 3.24 (m, 2H), 3.15 (m, 1H), 2.93 (m, 1H), 2.35 (d, J=13.8 Hz, 1H), 2.24 (m, 1H), 2.10 (m, 3H), 1.93 (m, 2H), 1.39 (m, 5H); $^{13}$C NMR (CDCl$_3$, 75 MHz): δ 194.5, 162.2, 148.5, 128.9, 128.4, 114.3, 112.6, 79.7, 72.9, 72.7, 66.7, 47.0, 45.3, 44.5, 40.9, 38.4, 36.3, 26.0, 25.9. Anal. Calcd. for C$_{19}$H$_{21}$NO$_2$.0.5HCl C, 72.77; H, 6.91; N, 4.47. Found: C, 72.66; H, 6.81; N, 4.30. For 3-Hydroxy-10-keto-N-cyclobutylmethylmorphinan 74: Pale-yellow solid (47%). Mp: 194-195° C. (Dec.); MS: m/e 325 (M+); $^1$H NMR (CDCl$_3$, 300 MHz): δ 7.98 (d, J=8.1 Hz, 1H), 6.77 (m, 2H), 3.99 (m, 1H), 3.05 (m, 1H), 2.59 (m, 3H), 2.30 (m, 2H), 2.05 (m, 4H), 1.62 (m, 12H); $^{13}$C NMR (CDCl$_3$, 75 MHz): δ 194.7, 162.4, 148.6, 128.8, 128.4, 114.2, 112.5, 67.3, 61.7, 46.9, 45.9, 41.0, 38.5, 36.4, 33.9, 27.9, 27.0, 26.0, 24.8, 21.9, 18.7. Anal. Calcd. for C$_{21}$H$_{27}$NO$_2$.0.5H$_2$O C, 75.41; H, 8.44; N, 4.19. Found C, 75.27; H, 8.17; N, 4.16. For 3-Hydroxy-10-keto-N-(3-fluoropropyl)morphinan 75: Pale-yellow solid (54.0%). Mp: 207-208° C.; MS: m/e 317 (M+); $^1$H NMR (CDCl$_3$, 300 MHz): δ 7.99 (d, J=8.4 Hz, 1H), 6.77 (m, 2H), 4.26 (m, 2H), 3.11 (s, 1H), 2.70 (m, 3H), 2.89 (m, 3H), 2.00 (m, 4H), 1.51 (m, 8H); $^{13}$C NMR (CDCl$_3$, 75 MHz): δ 194.8, 161.9, 148.4, 128.6, 128.4, 113.9, 112.3, 82.1 (d, J=163.0 Hz), 65.9, 50.6, 46.8, 45.9, 40.9, 38.3, 36.1, 27.9, 27.7, 25.8, 21.6. Anal. Calcd. for C$_{19}$H$_{24}$FNO$_2$.0.1H$_2$O C, 71.49; H, 7.64; N, 4.39. Found C, 71.29; H, 7.76; N, 4.46. For 3-Hydroxy-10-keto-N-(2-methoxyethyl)morphinan 76: White solid (56.5%). Mp: 196-197° C.; MS: m/e 315 (M+); $^1$H NMR (CDCl$_3$, 300 MHz): δ 7.97 (d, J=8.4 Hz, 1H), 6.79 (m, 2H), 3.58 (m, 2H), 3.34 (s, 3H), 3.12 (s, 1H), 2.81 (m, 2H), 2.54 (m, 1H), 2.08 (m, 4H), 1.36 (m, 8H); $^{13}$C NMR (CDCl$_3$, 75 MHz): δ 195.2, 163.1, 148.6, 128.7, 127.8, 114.4, 112.6, 69.4, 66.4, 58.7, 54.4, 46.6, 46.3, 40.8, 38.3, 36.3, 26.0, 21.9. Anal. Calcd. for C$_{19}$H$_{25}$NO$_3$.0.5H$_2$O C, 70.34; H, 8.08; N, 4.32. Found C, 70.35; H, 7.77; N, 4.30. For 3-Hydroxy-10-keto-N-(2-phenylethyl)morphinan 77: Pale-yellow solid (50.6%). Mp: 183-184° C.; MS: m/e 361 (M+); $^1$H NMR (CDCl$_3$, 300 MHz): δ 7.92 (d, J=8.4 Hz, 1H), 7.23 (m, 5H), 6.76 (m, 2H), 3.17 (s, 1H), 3.00 (d, J=14.7 Hz, 1H), 2.52 (m, 5H), 2.02 (m, 3H), 1.35 (m, 8H); $^{13}$C NMR (CDCl$_3$, 75 MHz): δ 195.0, 163.4, 148.3, 139.9, 128.5, 128.4, 128.3, 128.1, 127.8, 125.7, 113.8, 113.6, 112.3, 66.0, 57.1, 48.6, 46.8, 46.2, 40.8, 38.3, 36.2, 33.5, 25.9, 21.7. Anal. Calcd. for C$_{24}$H$_{27}$NO$_2$ C, 79.74; H, 7.53; N, 3.87. Found C, 79.39; H, 7.41; N, 3.86.

EXAMPLE 20

$K_i$ Values for μ, δ, and κ Binding of 10-ketomorphinans to CHO Membranes.

Four 10-ketomorphinan compounds, see Table 2, were evaluated for their affinity and selectivity at the three opioid receptors. As described in Example 12, 0.5 milligrams of protein per sample was incubated with 12 different concentrations of the compounds in the presence of receptor-specific radioligands at 25° C. in a final volume of 1 mL (50 mM Tris-HCl buffer, pH 7.5). Nonspecific binding was determined using 10 μM naloxone. The data in Table 2 are the mean values SEM from three experiments performed in triplicate.

TABLE 2

| Com- pound | [$^3$H]DAMGO (μ) | [$^3$H]Naltrin- dole (δ) | [$^3$H]U69,593 (κ) | Selectivity μ:κ | δ:κ |
|---|---|---|---|---|---|
| 73 | 190 ± 4.4 | 2300 ± 190 | 60 ± 1.7 | 3.2 | 38 |
| 74 | 3.3 ± 0.26 | 260 ± 55 | 0.48 ± 0.027 | 6.9 | 540 |
| 75 | 20 ± 4.8 | 690 ± 171 | 2.5 ± 0.42 | 8.0 | 280 |
| 76 | 90 ± 10 | >10 μM | 17 ± 0.60 | 5.3 | 590 |
| 77 | 0.63 ± 0.07 | 9.7 ± 0.34 | 7.7 ± 0.19 | 0.08 | 1.3 |

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A compound of formula I:

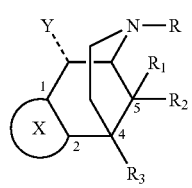

(I)

or a pharmaceutically acceptable salt thereof, wherein X includes the carbon atoms at positions 1 and 2 and is selected from

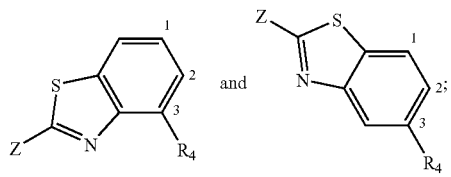

Y is H, oxo, or methyl;

R is selected from H, C$_{1-7}$ alkyl, C$_{2-7}$ alkenyl, C$_{2-7}$ alkynyl, C$_{2-6}$ heterocyclyl, C$_{6-12}$ aryl, C$_{7-14}$ alkaryl, C$_{3-10}$ alkheterocyclyl, and C$_{1-7}$ heteroalkyl;

R$_1$ is H;

R$_4$ is H and R$_2$ and R$_3$ combine to form a fused six-membered ring in which position 4 is connected to position 5 by

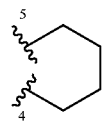

Z is —NHR$_5$; and

R$_5$ is H.

2. The compound of claim 1, wherein said compound is described by formulas II or III:

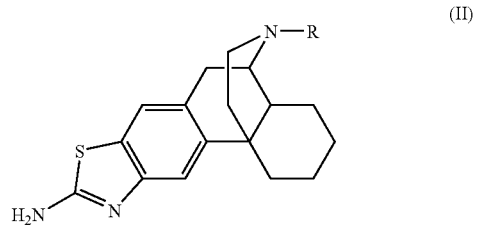

(II)

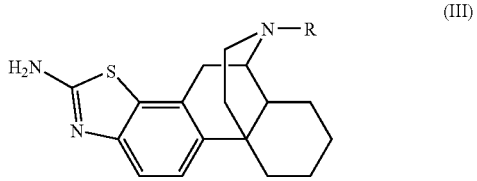

(III)

or a pharmaceutically acceptable salt thereof, wherein R is selected from H, C$_{1-7}$ alkyl, C$_{2-7}$ alkenyl, C$_{2-7}$ alkynyl, C$_{2-6}$ heterocyclyl, C$_{6-12}$ aryl, C$_{7-14}$ alkaryl, C$_{3-10}$ alkheterocyclyl, and C$_{1-7}$ heteroalkyl.

3. The compound of claim 1, wherein said compound is described by formula IX:

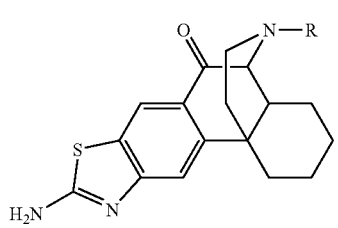

(IX)

or a pharmaceutically acceptable salt thereof, wherein R is selected from H, $C_{1-7}$ alkyl, $C_{2-7}$ alkenyl, $C_{22-7}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl.

4. The compound of claim 2 or 3, wherein R is selected from $CH_3$, $CH_2(cyclo-C_4H_7)$, $CH_2(cyclo-C_3H_5)$, $CH(CH_3)(cyclo-C_3H_5)$, $CH_2CH_2CH_2F$, $CH_2CH_2OCH_3$, $CH_2CH_2OCF_3$, $CH_2CH(CH_3)_2$, $CH_2CH=CH_2$, trans-$CH_2CH=CHI$, $CH_2C\equiv CH$, benzyl, phenethyl, 3,4-dichlorophenethyl, 3-furanylmethyl, 2-furanylmethyl, 3-tetrahydrofuranylmethyl, and 2-tetrahydrofuranylmethyl.

5. The compound of claim 4, wherein said compound has the structure

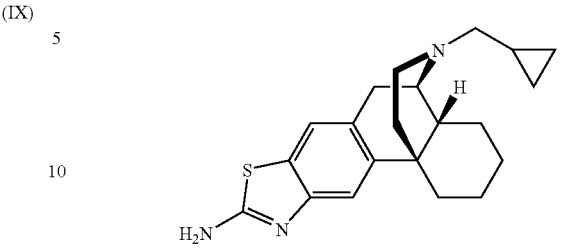

or a pharmaceutically acceptable salt thereof.

6. A pharmaceutical composition comprising an effective amount of a compound of any of claims 1, 2, 3, or 5, or a suitable salt thereof together with a pharmaceutically acceptable carrier or diluent.

7. A method of treating pain in a patient in need thereof, said method comprising the step of administering to said patient a pharmaceutical composition of claim 6 in an amount sufficient to treat said pain.

* * * * *

UNITED STATES PATENT AND TRADEMARK OFFICE
CERTIFICATE OF CORRECTION

PATENT NO. : 7,271,173 B2
APPLICATION NO. : 10/716100
DATED : September 18, 2007
INVENTOR(S) : Neumeyer et al.

It is certified that error appears in the above-identified patent and that said Letters Patent is hereby corrected as shown below:

On Title Page, item (56); under OTHER PUBLICATIONS, in Kaczor and Matosiuk,
    replace "Recptor" with --Receptor--;

Under OTHER PUBLICATIONS, in Ucar et al., replace
"Selective δ" with --Selective σ--;

Title Page, item (57); under ABSTRACT, replace "attention deficit hyperactivity
    disorder (ADD)" with
    --attention deficit disorder (ADD)--.

Column 1, Line 53-54, replace "attention deficit hyperactivity
    disorder (ADD)" with --attention deficit disorder (ADD)--.

Column 5, Line 61, replace "attention deficit hyperactivity
    disorder (ADD)" with --attention deficit disorder (ADD)--.

Column 6, Line 61, replace "attention deficit hyperactivity
    disorder (ADD)" with --attention deficit disorder (ADD)--.

Column 10, Line 40, replace "R is is selected" with
    --R is selected--.

Column 11, Line 21, replace "attention deficit hyperactivity
    disorder (ADD)" with --attention deficit disorder (ADD)--.

Column 12, Line 58, replace "attention deficit hyperactivity
    disorder (ADD)" with --attention deficit disorder (ADD)--.

Signed and Sealed this
Twenty-seventh Day of November, 2012

David J. Kappos
*Director of the United States Patent and Trademark Office*

CERTIFICATE OF CORRECTION (continued)
U.S. Pat. No. 7,271,173 B2

Column 21, Reagents: b)., replace "ClCl$_2$CH2NMe$_2$, NaH;" with
--ClCl$_2$CH$_2$NMe$_2$, NaH;--;

Reagents: d)., replace "NH4OH, then acetone;" with
--NH$_4$OH, then acetone;--.

Column 21, Line 24, replace "N-phenyl bis(trifluoromethanesulfonimide, yields" with --N-phenyl bis(trifluoromethanesulfonimide), yields--.

Column 22, Line 25, replace "Wolfe etal.," with
--Wolfe et al.,--.

Column 31, Line 42, replace "(2003)." with --(2003)).--;

Line 51, replace "(2000)." with --(2000)).--;

Column 39, Line 53, replace "Na2SO4" with --Na$_2$SO$_4$--.

Column 43, Claim 3, Line 16, replace "C$_{22-7}$ alkynyl" with
--C$_{2-7}$ alkynyl--.